(12) United States Patent
Jones et al.

(10) Patent No.: US 11,653,926 B2
(45) Date of Patent: May 23, 2023

(54) CIRCULAR SURGICAL STAPLER FOR FORMING PATTERN OF NON-TANGENTIAL STAPLES

(71) Applicant: Cilag GmbH International, Zug (CH)

(72) Inventors: Shannon L. Jones, Cincinnati, OH (US); Gregory J. Bakos, Mason, OH (US); Jeffery Bruns, Cincinnati, OH (US); Ryan W. McGhee, Cincinnati, OH (US); Scott A. Jenkins, Mason, OH (US); Laura S. Downing, Cincinnati, OH (US); John E. Feds, Milford, OH (US); Maxwell T. Rockman, Cincinnati, OH (US); John E. Brady, Liberty Township, OH (US); Ravi Patel, East Providence, RI (US); Aaron C. Voegele, Loveland, OH (US); Austin J. Bridges, Huntington Beach, CA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/401,444

(22) Filed: Aug. 13, 2021

(65) Prior Publication Data

US 2023/0053080 A1 Feb. 16, 2023

(51) Int. Cl.
*A61B 17/064* (2006.01)
*A61B 17/115* (2006.01)
(Continued)

(52) U.S. Cl.
CPC ....... *A61B 17/1155* (2013.01); *A61B 17/1114* (2013.01); *A61B 2017/07228* (2013.01);
(Continued)

(58) Field of Classification Search
CPC .................. A61B 17/1155; A61B 2017/07257
See application file for complete search history.

(56) References Cited

U.S. PATENT DOCUMENTS

| | | | |
|---|---|---|---|
| 4,047,654 A | 9/1977 | Alvarado | |
| 4,848,328 A * | 7/1989 | Laboureau | A61B 17/0642 606/75 |

(Continued)

FOREIGN PATENT DOCUMENTS

| | | |
|---|---|---|
| EP | 1875870 A1 | 1/2008 |
| EP | 2157918 A0 | 3/2010 |

(Continued)

OTHER PUBLICATIONS

U.S. Appl. No. 17/401,391.

(Continued)

*Primary Examiner* — Eyamindae C Jallow
(74) *Attorney, Agent, or Firm* — Frost Brown Todd LLP

(57) ABSTRACT

A surgical stapling instrument includes an anvil and a stapling head assembly. The anvil defines staple forming pockets. The stapling head assembly includes a body, a coupling member, a firing assembly, and a staple deck. The coupling member is configured to actuate relative to the body to thereby acuate the anvil relative to the body. The firing assembly is configured to drive staples against the staple forming pockets of the anvil. The staple deck is defined by an outer arched perimeter and an inner arched perimeter fixed to the body. The staple deck defines staple openings. At least one non-tangential staple opening in the of staple openings extends along a longitudinal axis in a non-tangential relationship with a closest tangent line of the inner arched perimeter or the outer arched perimeter.

19 Claims, 35 Drawing Sheets

(51) Int. Cl.
*A61B 17/11* (2006.01)
*A61B 17/072* (2006.01)

(52) U.S. Cl.
CPC .............. *A61B 2017/07264* (2013.01); *A61B 2017/07285* (2013.01); *A61B 2017/1132* (2013.01)

(56) References Cited

U.S. PATENT DOCUMENTS

| | | | |
|---|---|---|---|
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 6,616,686 | B2 * | 9/2003 | Coleman ............ A61B 17/1285 606/221 |
| 7,056,330 | B2 * | 6/2006 | Gayton .............. A61B 17/0644 606/139 |
| 7,422,138 | B2 | 9/2008 | Bilotti et al. |
| 7,824,426 | B2 | 11/2010 | Racenet et al. |
| 8,143,870 | B2 | 3/2012 | Ng et al. |
| 8,328,063 | B2 | 12/2012 | Milliman et al. |
| 8,613,384 | B2 | 12/2013 | Pastorelli et al. |
| 8,789,738 | B2 | 7/2014 | Knodel et al. |
| 8,910,847 | B2 | 12/2014 | Nalagatla et al. |
| 9,016,541 | B2 | 4/2015 | Viola et al. |
| 9,192,387 | B1 | 11/2015 | Holsten et al. |
| 9,402,628 | B2 | 8/2016 | Beardsley |
| 9,713,469 | B2 | 7/2017 | Leimbach et al. |
| 9,782,171 | B2 | 10/2017 | Viola |
| 9,848,874 | B2 | 12/2017 | Kostrzewski |
| 9,907,552 | B2 | 3/2018 | Measamer et al. |
| 9,936,949 | B2 | 4/2018 | Measamer et al. |
| 10,639,040 | B2 | 5/2020 | Penna et al. |
| 10,709,452 | B2 | 7/2020 | DiNardo et al. |
| 11,147,559 | B2 | 10/2021 | Wise et al. |
| 11,291,450 | B2 | 4/2022 | Nalagatla et al. |
| 11,523,821 | B2 | 12/2022 | Harris et al. |
| 2006/0291981 | A1 | 12/2006 | Viola et al. |
| 2011/0011916 | A1 | 1/2011 | Levine |
| 2014/0027493 | A1 | 1/2014 | Jankowski |
| 2014/0158747 | A1 | 6/2014 | Measamer et al. |
| 2015/0083772 | A1 | 3/2015 | Miller et al. |
| 2016/0278768 | A1 | 9/2016 | Johnson et al. |
| 2017/0119397 | A1 | 5/2017 | Harris et al. |
| 2017/0281187 | A1 * | 10/2017 | Shelton, IV ....... A61B 17/1155 |
| 2017/0281188 | A1 * | 10/2017 | Shelton, IV ......... A61B 17/105 |
| 2017/0281189 | A1 * | 10/2017 | Nalagatla .......... A61B 17/3211 |
| 2018/0132849 | A1 * | 5/2018 | Miller .............. A61B 17/07207 |
| 2018/0206846 | A1 * | 7/2018 | Guerrera ............ A61B 17/1155 |
| 2018/0235635 | A1 | 8/2018 | Rekstad et al. |
| 2018/0242974 | A1 * | 8/2018 | Guerrera ............ A61B 17/1155 |
| 2018/0242975 | A1 * | 8/2018 | Penna ................... A61B 46/10 |
| 2018/0325508 | A1 | 11/2018 | Aronhalt et al. |
| 2020/0038017 | A1 | 2/2020 | Hess et al. |
| 2020/0054339 | A1 | 2/2020 | Scirica et al. |
| 2020/0229814 | A1 | 7/2020 | Amariglio et al. |

FOREIGN PATENT DOCUMENTS

| | | | |
|---|---|---|---|
| EP | 2649949 | A1 | 10/2013 |
| EP | 3225176 | A1 | 10/2017 |
| EP | 3225179 | A1 | 10/2017 |
| EP | 3245958 | A1 | 11/2017 |
| EP | 3130292 | B1 | 8/2018 |
| EP | 3173030 | B1 | 10/2019 |
| EP | 3643252 | A1 | 4/2020 |
| WO | WO 2001/054594 | A1 | 8/2001 |
| WO | WO 2002/009595 | A1 | 2/2002 |
| WO | WO 2005/115254 | A2 | 12/2005 |
| WO | WO 2008/141288 | A1 | 11/2008 |
| WO | WO 2020/249487 | A1 | 12/2020 |

OTHER PUBLICATIONS

U.S. Appl. No. 17/401,428.
U.S. Appl. No. 17/401,430.
U.S. Appl. No. 17/401,439;.
U.S. Appl. No. 17/401,451; and.
U.S. Appl. No. 17/401,460.
U.S. Appl. No. 17/401,391, entitled, "Methods of Forming an Anastomosis Between Organs with an Expandable Pattern," filed Aug. 13, 2021.
U.S. Appl. No. 17/401,428, entitled, "Staple Forming Features for Circular Surgical Stapler," filed Aug. 13, 2021.
U.S. Appl. No. 17/401,430, entitled, "Non-Circular End Effector Features for Surgical Stapler," filed Aug. 13, 2021.
U.S. Appl. No. 17/401,439, entitled, "Circular Surgical Stapler End Effector Having Staple Line Alignment Feature," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,460, entitled, "Circular Surgical Stapler for Forming Cross-Pattern of Staples," filed Aug. 13, 2021.
International Search Report and Written Opinion dated Nov. 14, 2022 for Application No. PCT/IB2022/057444, 12 pgs.
International Search Report and Written Opinion dated Jan. 27, 2023 for Application No. PCT/IB2022/057446, 19 pgs.
International Search Report and Written Opinion dated Nov. 23, 2022 for Application No. PCT/IB2022/057449, 15 pgs.
International Search Report and Written Opinion dated Jan. 25, 2023 for Application No. PCT/IB2022/057442, 20 pgs.
International Search Report and Written Opinion dated Nov. 14, 2022 for Application No. PCT/IB2022/057443, 12 pgs.
International Search Report and Written Opinion dated Nov. 24, 2022 for Application No. PCT/IB2022/057451, 13 pgs.

* cited by examiner

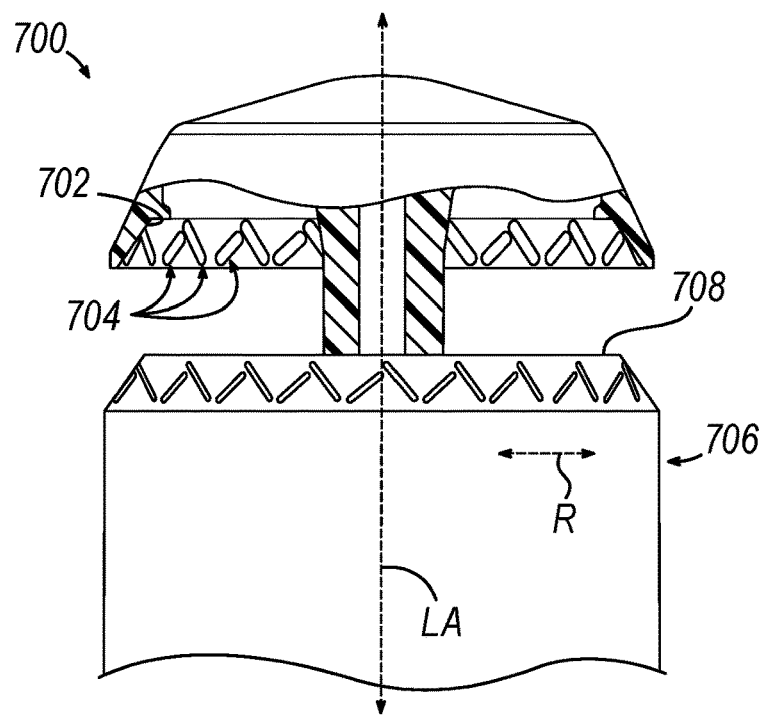
FIG. 27
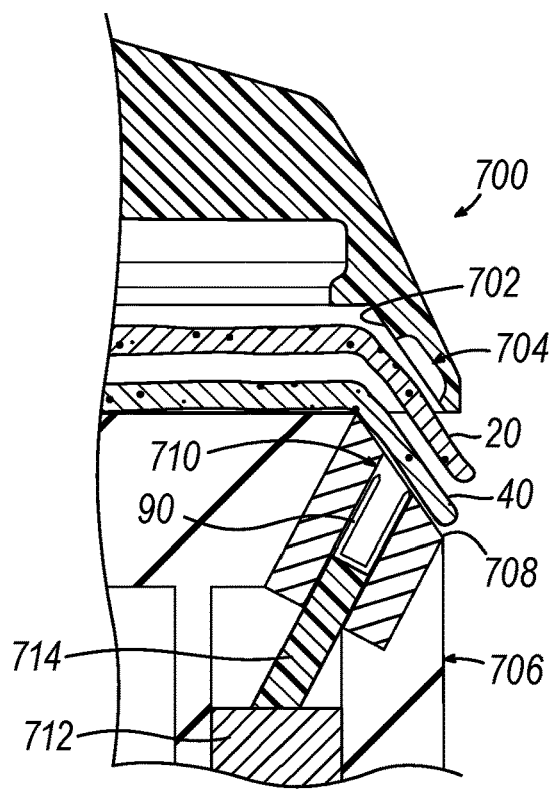 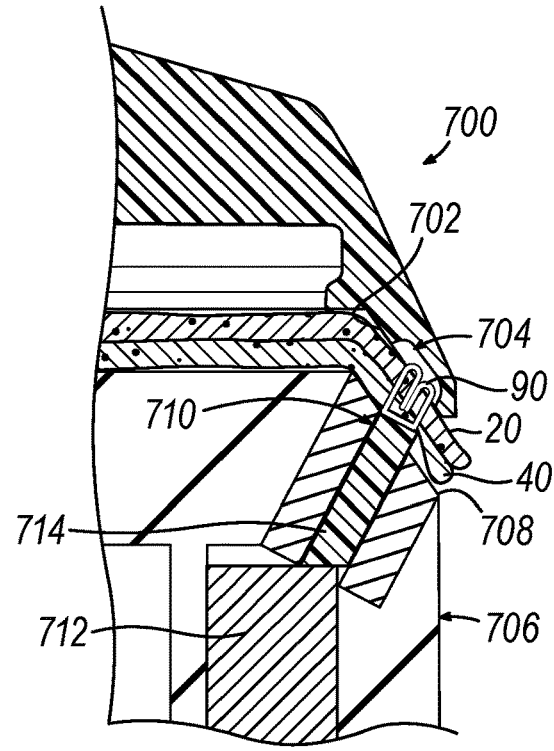
FIG. 28A  FIG. 28B

CIRCULAR SURGICAL STAPLER FOR FORMING PATTERN OF NON-TANGENTIAL STAPLES

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 27 depicts a front elevational view of an alternative exemplary anvil and an alternative exemplary stapling head assembly that may be incorporated into the circular stapler of FIG. 1;

FIG. 28A depicts a cross-sectional view of the anvil and stapling head assembly of FIG. 27 initially grasping tissue and in a pre-fired position;

FIG. 28B depicts a cross-sectional view of the anvil and stapling head assembly of FIG. 27 grasping tissue an in a fired position;

Figure 1:
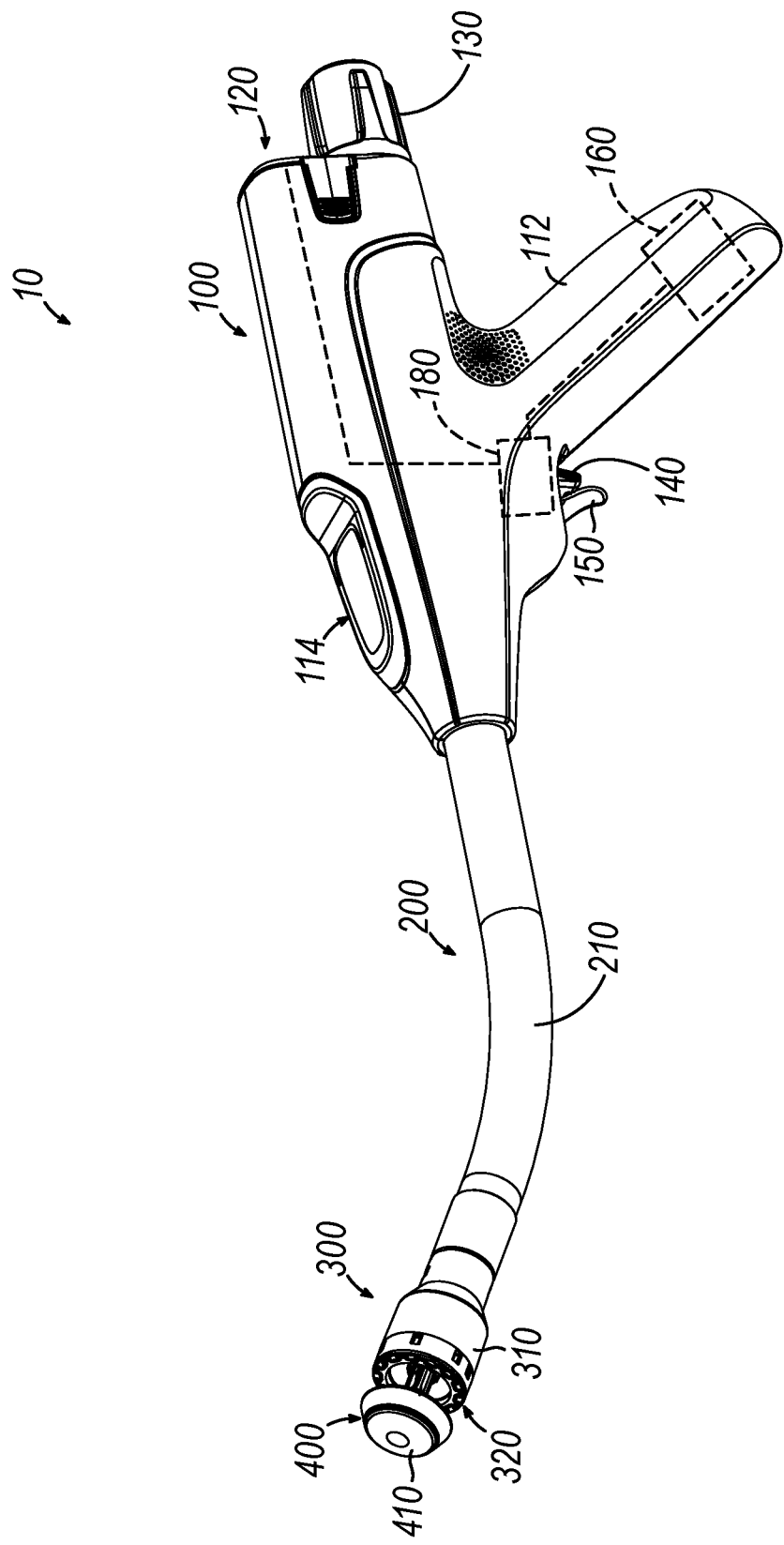
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. OVERVIEW OF EXEMPLARY CIRCULAR SURGICAL STAPLING INSTRUMENT

Figure 2:
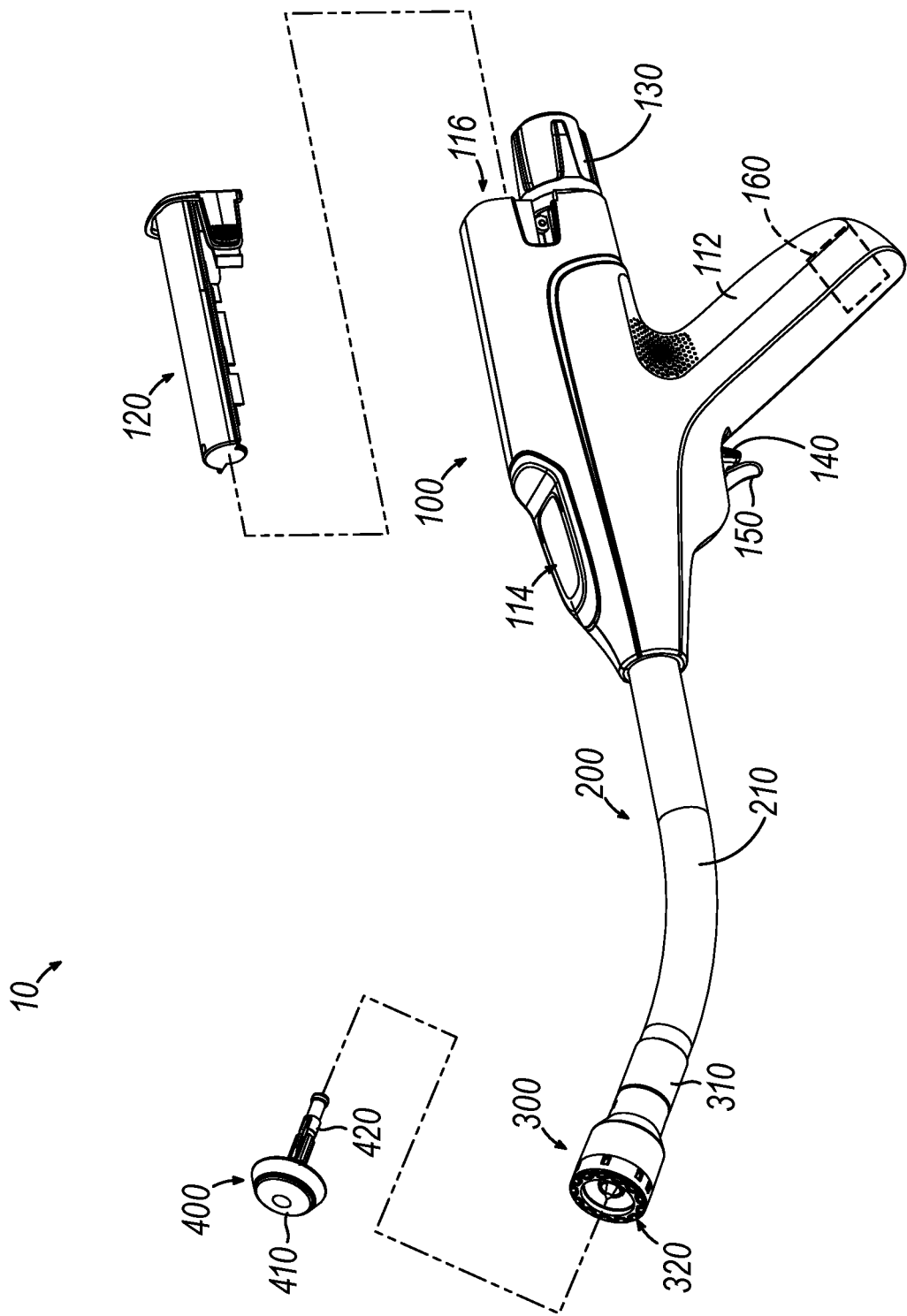
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
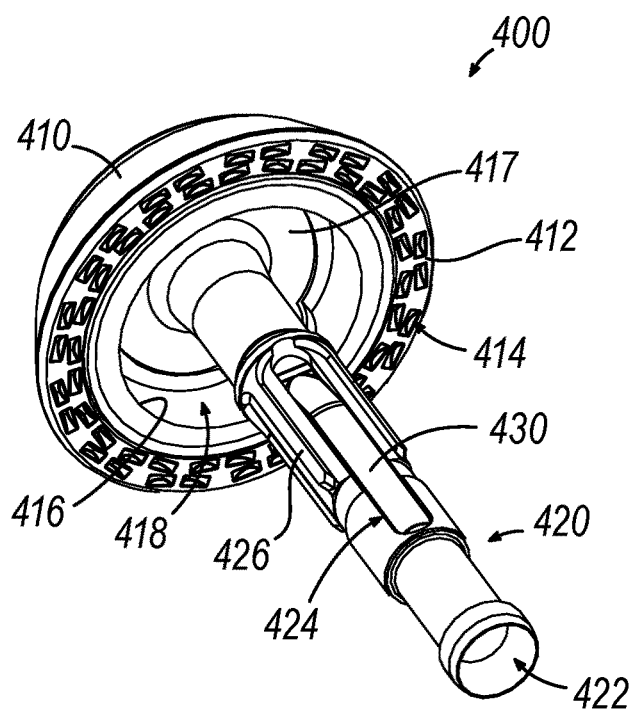
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
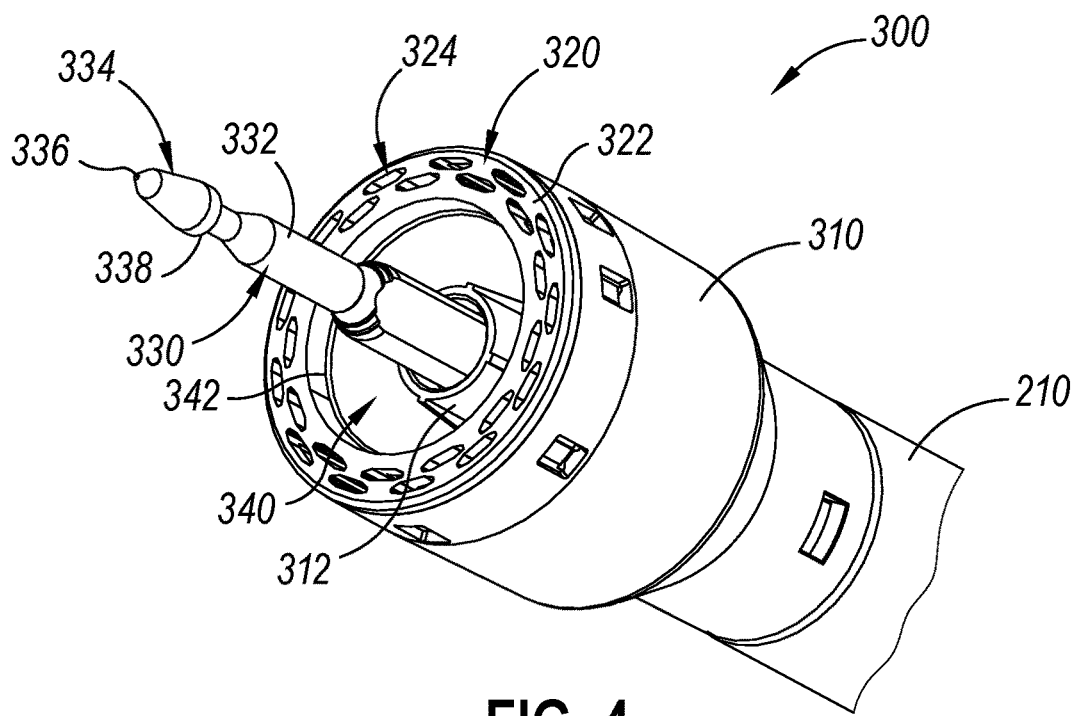
FIG. 4 depicts a perspective view of the stapling head assembly of the circular stapler of FIG. 1.
Figure 5:
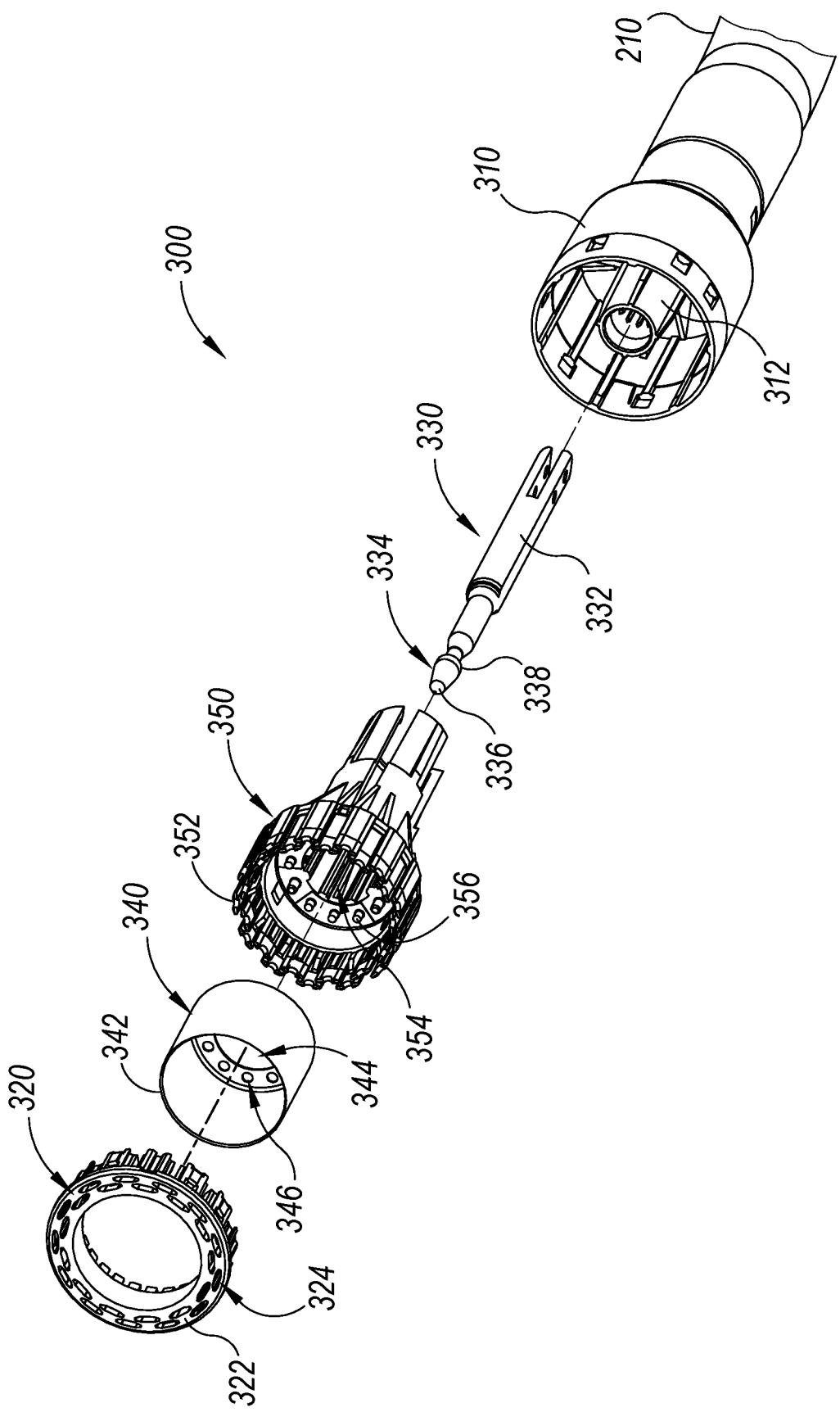
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

Figure 9:
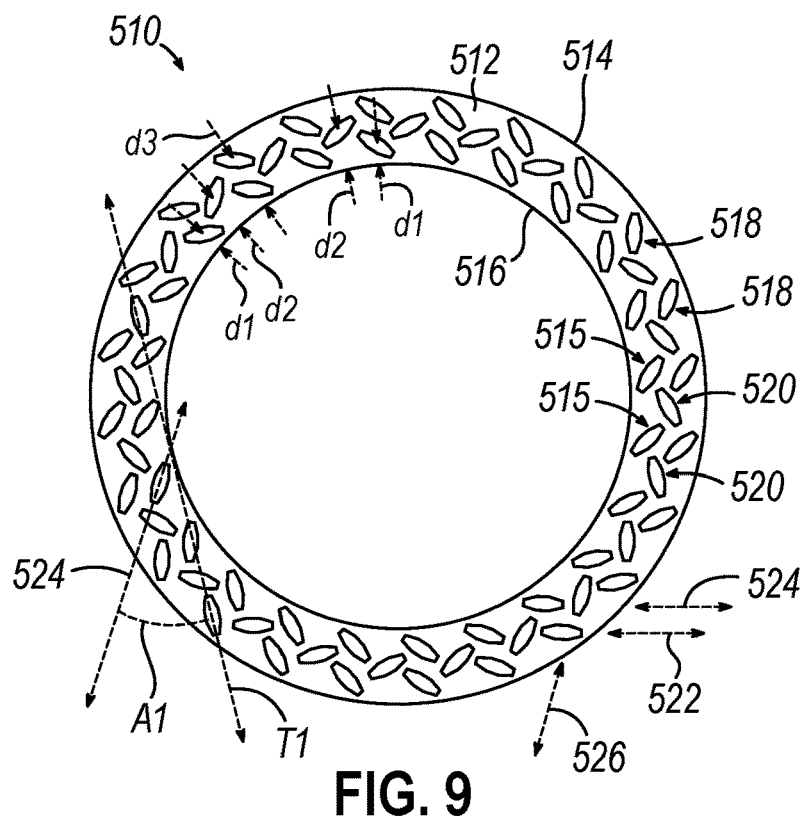
FIG. 9 depicts a top plan view of an alternative deck member that may be incorporated into the stapling head assembly of FIG. 4.

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 9, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
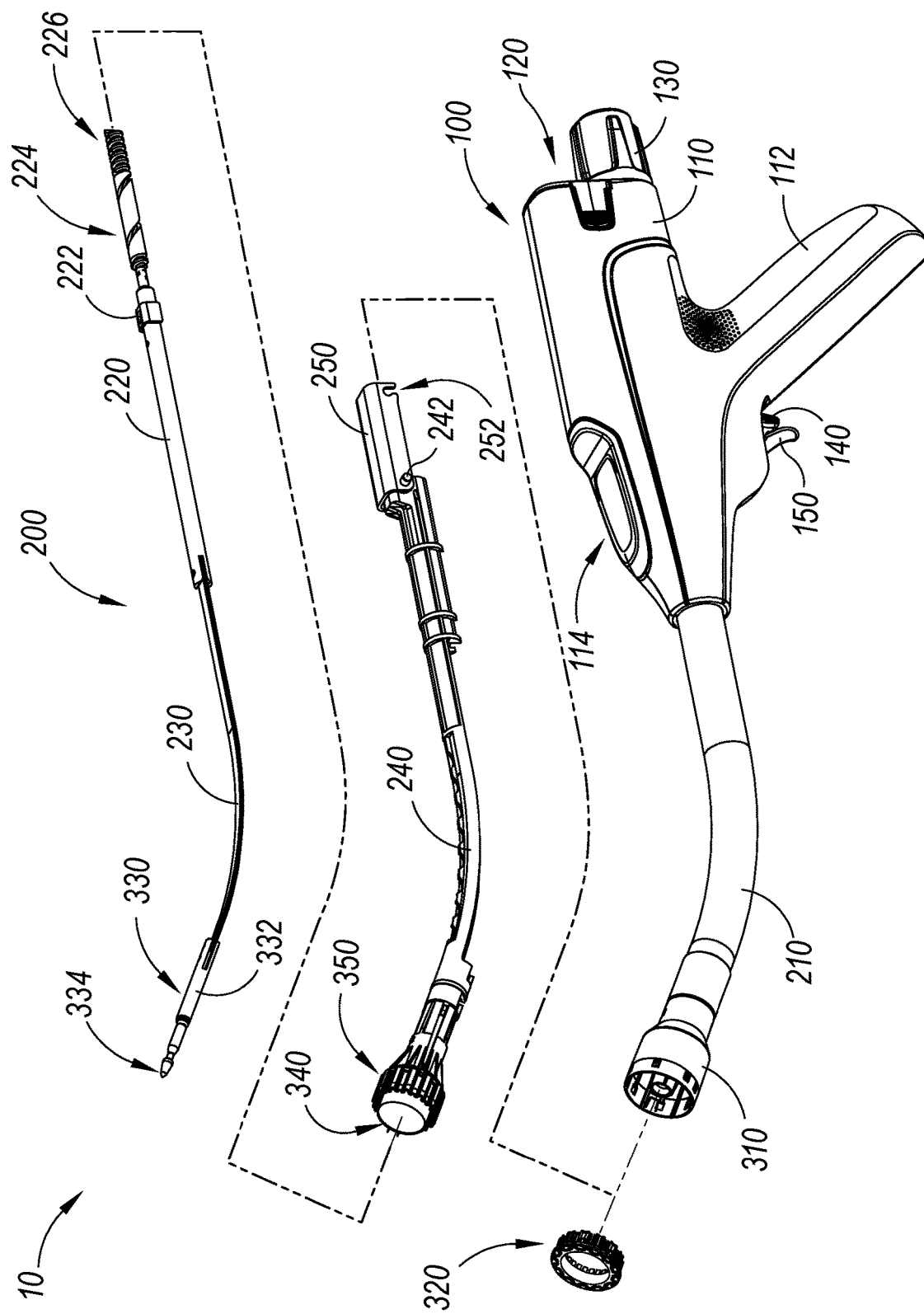
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150)

is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
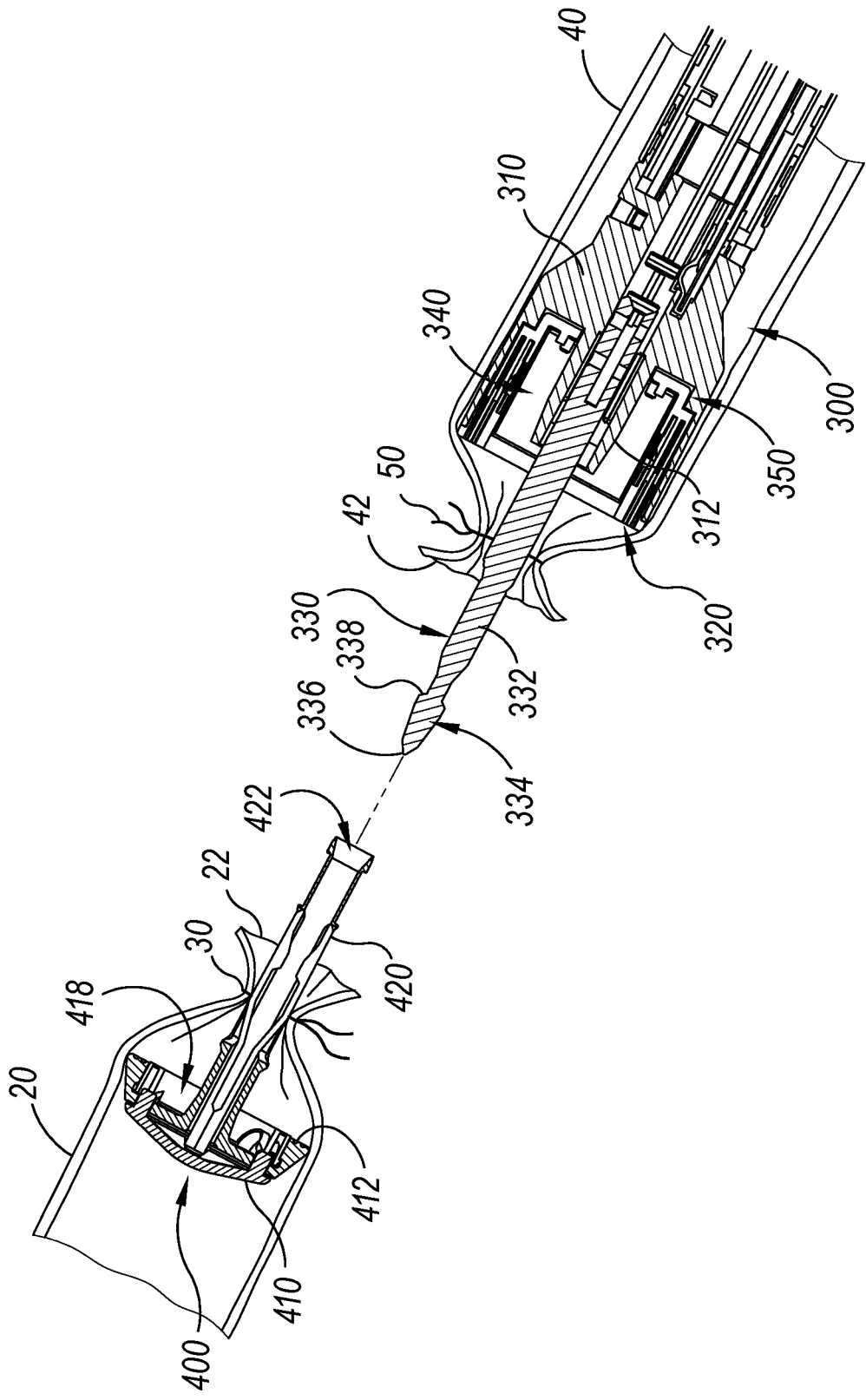
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
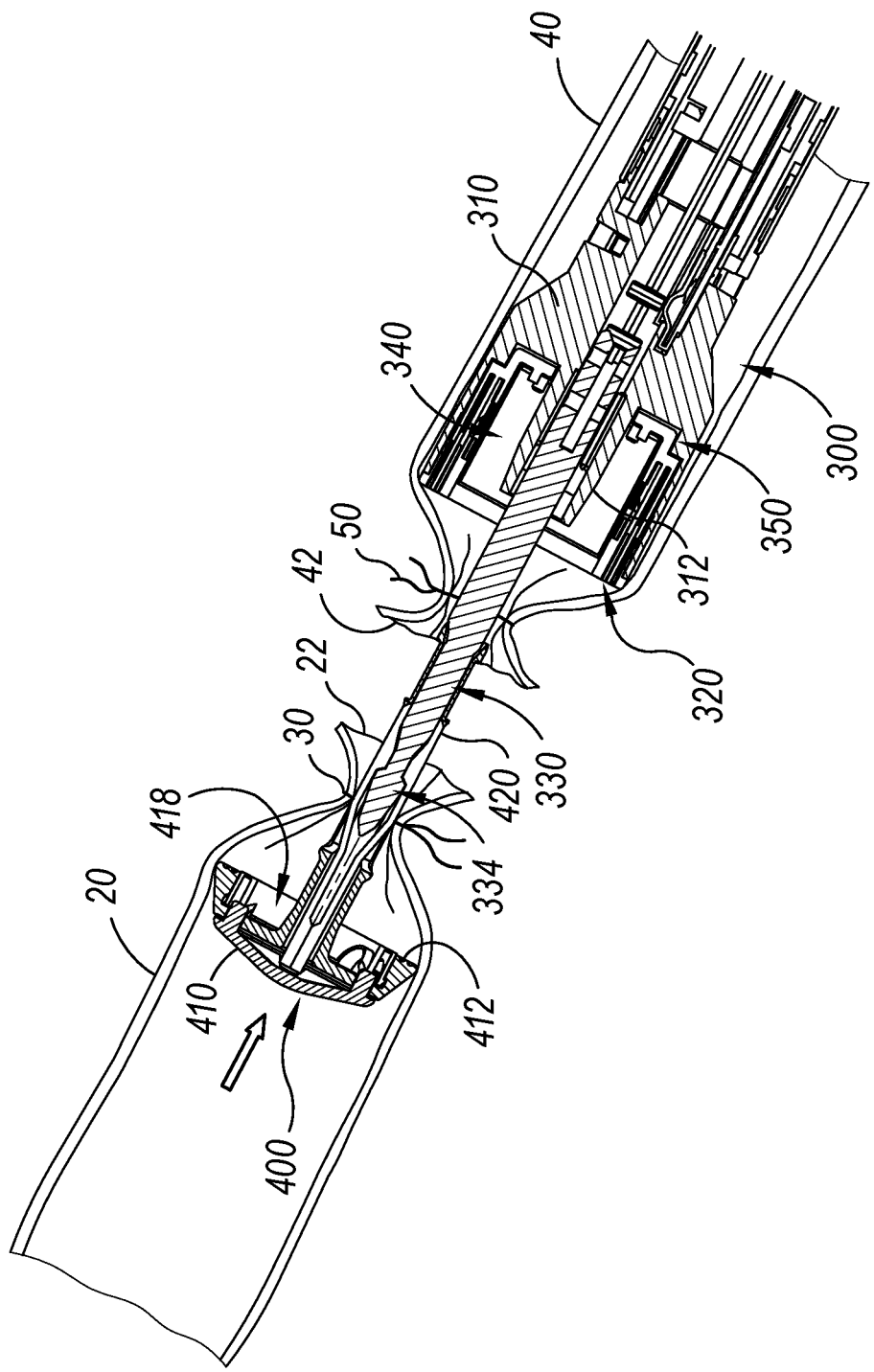
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
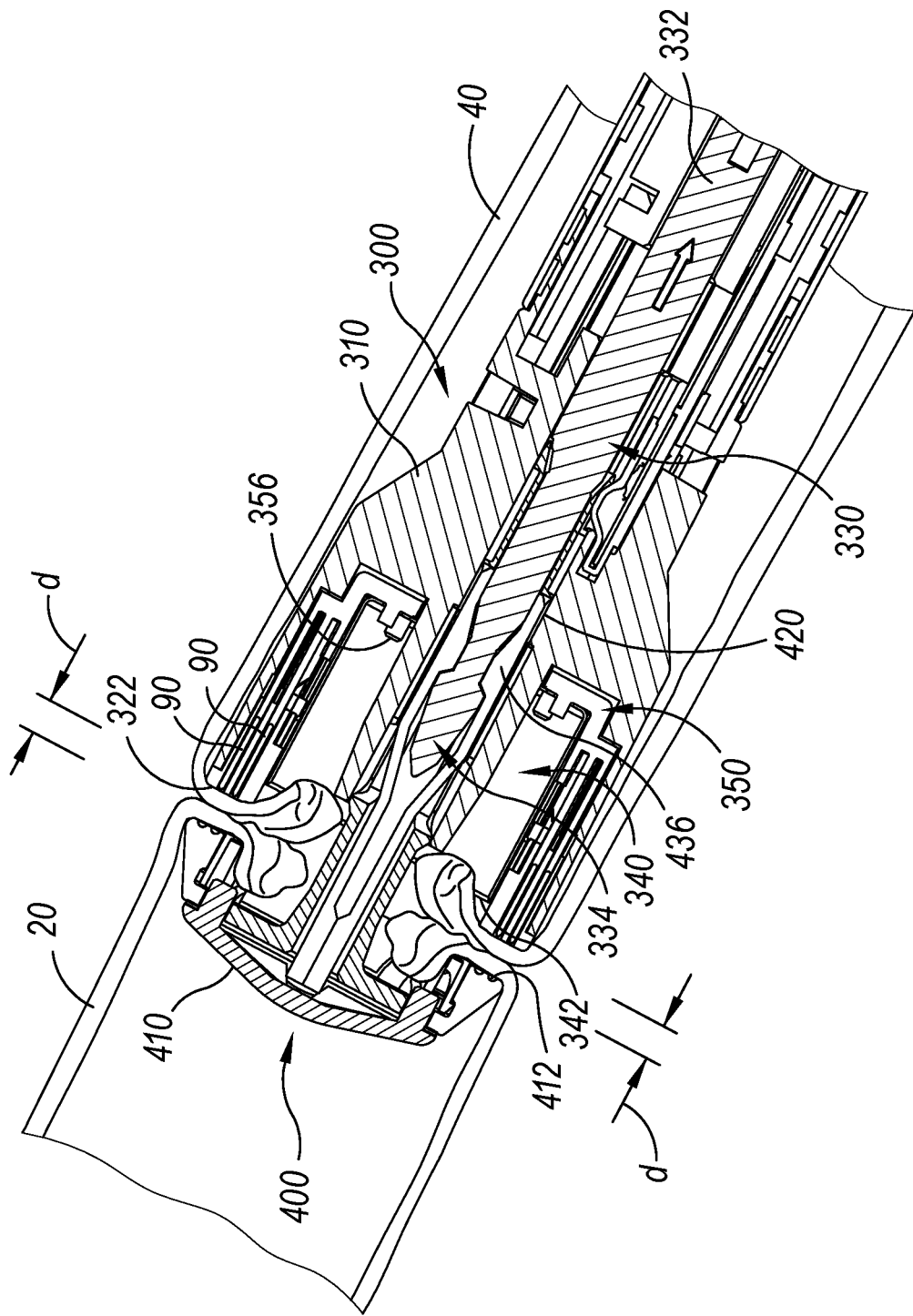
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
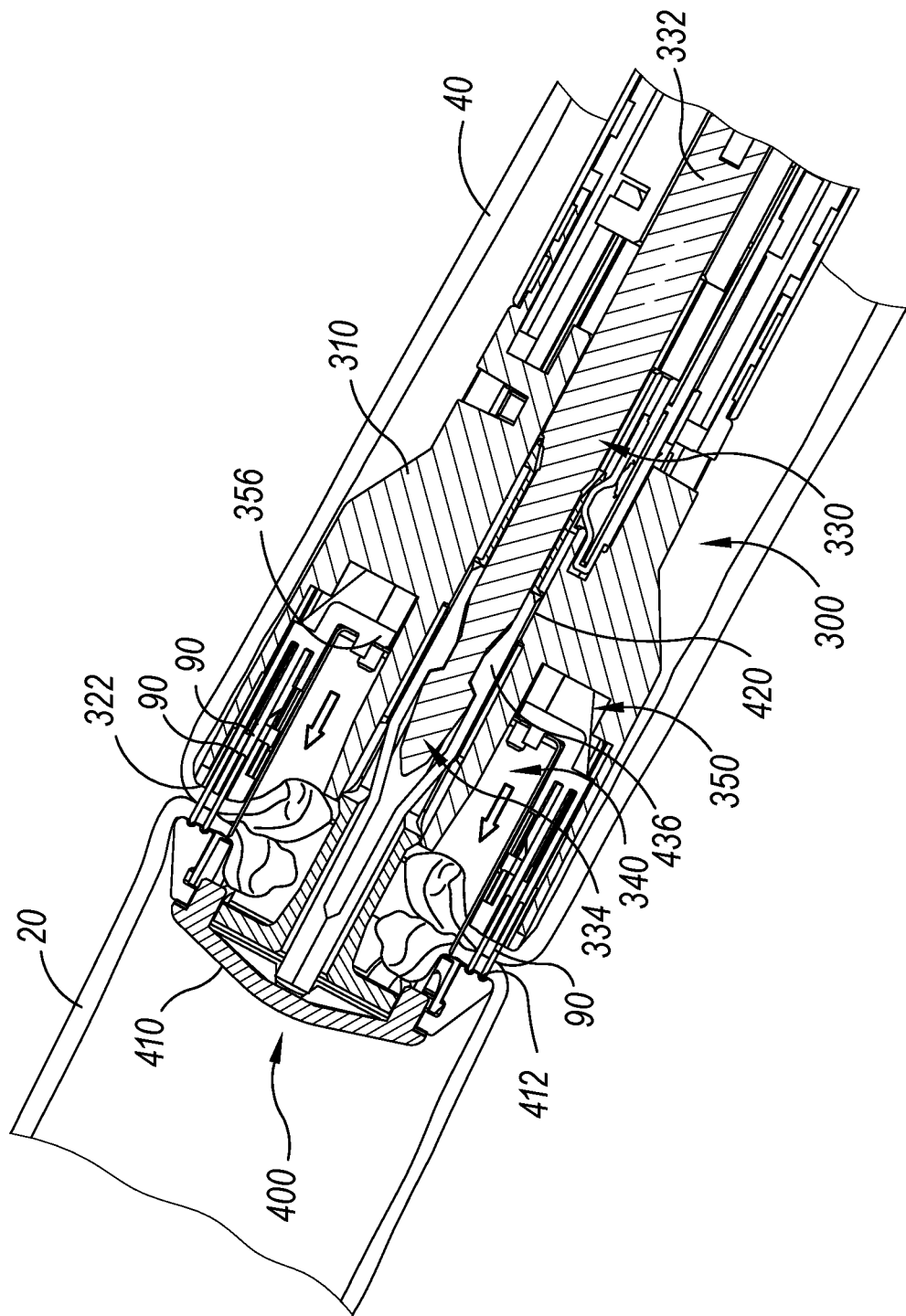
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
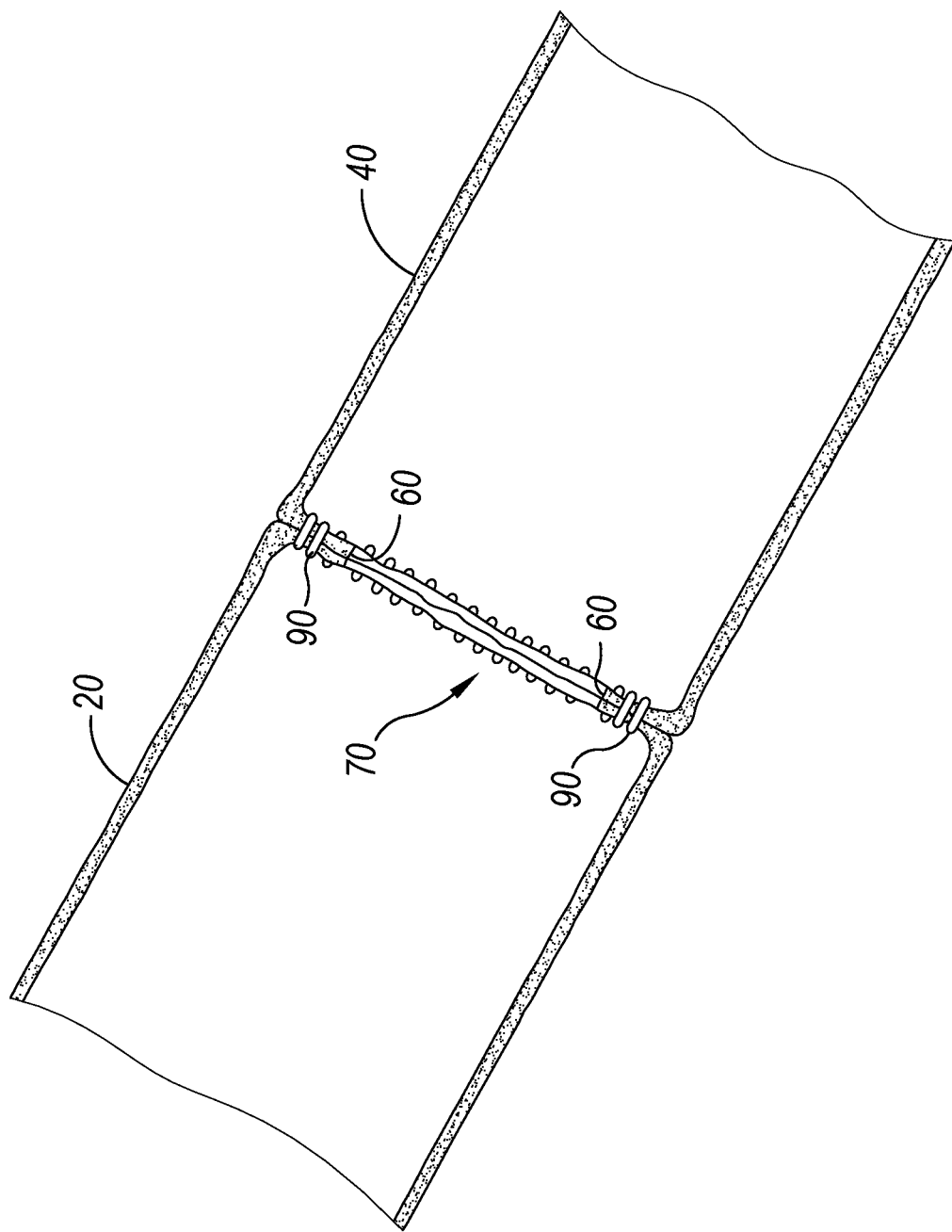
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. EXEMPLARY STAPLER FEATURES FOR FORMING NON-TANGENTIAL STAPLE PATTERNS

In some scenarios, the tissue forming the tubular anatomical structures (20, 40) may need to expand and contract in the radial direction after being stapled together as described above. For instance, when structures (20, 40) are organ portions of a patient's digestive tract, those organ portions may need to expand and contract during peristalsis to accommodate passage of digestive matter (e.g., chyme, waste products of the digestive process, stool, etc.). Therefore, the portion of the tubular anatomical structures (20, 40) that are stapled together may need to withstand such expansion and contraction while also maintaining the structural integrity of the staples (90) and the tissue at the staples (90), to continue suitably securing the ends of anatomical structures (20, 40) together.

The configuration and/or arrangement of formed staples (90) may restrict the ability of anastomosis (70) to expand radially in some cases. Therefore, it may be desirable to incorporate a staple pattern or staples that in turn enhance the structural integrity of the stapled ends of the anatomical structures (20, 40), thereby better accommodating for such expansion and contraction during peristalsis or other normal anatomical functioning.

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) may be generally smaller than that of each tubular anatomical structure (20, 40). In other words, anastomosis (70) and severed edges (60) extend radially inwardly within the interior of the tubular anatomical structure (20, 40). With severed edges (60) extending radially inwardly, such severed edges (60) may act as an obstruction for the passage of digestive matter. If such an obstruction becomes too great, it may negatively impact the patient's ability to digest food, or even damage the integrity of stapled tissue (20, 40). Therefore, in order to minimize such obstructions, it may be desirable to a minimize the length to which severed edge (60) extends radially inwardly within the interior of tubular anatomic structure (20, 40).

Since staples (90) are fired in a longitudinal direction that is substantially parallel with the length of the adjacent anatomical structures (20, 40), and since knife member (340) is located radially inward from deck surface (22), the width of deck surface (22) (i.e., the distance between the inner diameter and outer diameter of deck surface (22)) may be a factor in the length to which severed edges (60) extend radially inwardly from structures (20, 40). Therefore, to the extent it may be desirable to alter the staple pattern formed by staple openings (324) defined by deck surface (322), it may also be desirable to minimize the width of deck surface (322) in order to accommodate such a change in staple pattern. Additionally, it may be desirable to minimize the width of deck surface (322) in the direction substantially perpendicular to the length of adjacent anatomical structures (20, 40) in order to reduce the length of severed edges (60) and the chance severed edges (60) become an undesirable obstruction.

In some procedures, it may be desirable to form an anastomosis (70) of enlarged diameter and/or to enable the annular arrays of formed staples (90) to expand radially outwardly, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). Exemplary versions of such features are described in greater detail below. The below described features may be readily incorporated into instrument (10), such that a modified version of instrument (10) may include any one or more of the various features described below.

A. Exemplary Alternative Staple Patterns and Staples

As shown in FIG. 4, staple openings (324) each have a length that extends along an axis that is parallel to the closest tangent line of the inner diameter or outer diameter of annular deck member (320). In order to better accommodate for radial expansion and contraction, as described above, it may be desirable to have a staple deck with at least some staple openings that have a length extending along an axis that forms a non-parallel relationship with the closest tangent line of either the inner diameter or outer diameter of deck member (320). It should be understood that a staple opening that extends long a length that forms a non-parallel relationship with the closest tangent line of either the inner or outer diameter of a deck member is considered a non-tangential staple opening housing a non-tangentially oriented staple. The length of a staple opening may be considered the portion of the staple opening in which the crown of a staple extends to connect to the legs of a staple.

Figure 8:
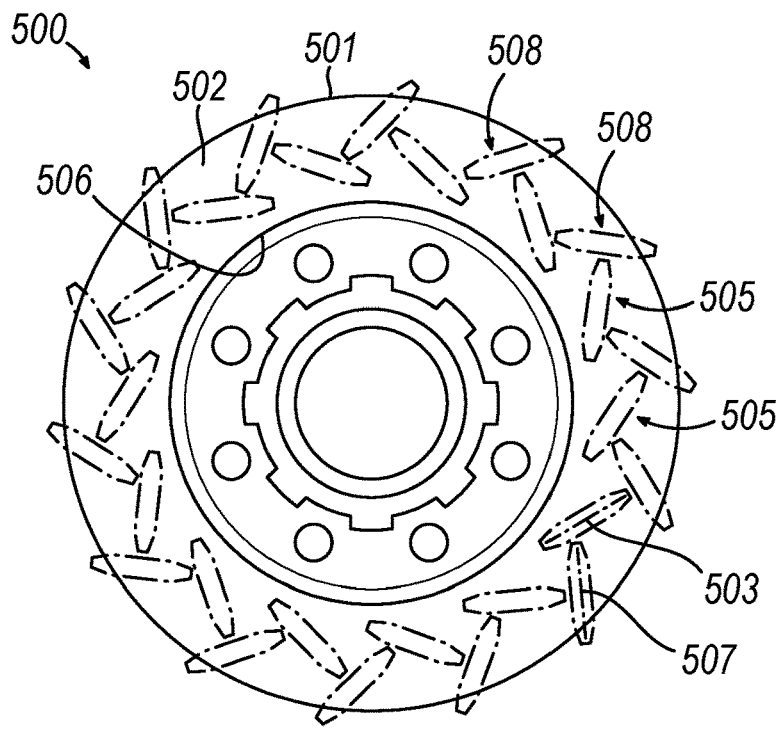
FIG. 8 depicts a top plan view of an alternative deck member that may be incorporated into the stapling head assembly of FIG. 4, the deck member defining an inner array of staple openings and an outer array of staple openings of uniform size, where the outer annular array is sized and arranged to not fit within the parameters of the deck member.

FIG. 8 shows an exemplary staple deck member (500) having a deck surface (502) defined by an outer diameter (504) and an inner diameter (506). Deck surface (502) attempts to define an outer array of stale openings (508) and an inner array of staple openings (505) forming a traditional herringbone pattern. Array of staple openings (505, 508) both having individual openings extending in a non-tangential relationship without modifying (A) the width of deck surface (502) or (B) the size of staple openings (505, 508) as compared to staple openings (324) described above. However, as best shown in how a portion of staple openings (508) extend past the outer diameter (504) of deck surface (502), staple openings (508, 505) are difficult to orient in a non-tangential relationship without undesirably increasing the width of deck surface (522).

Figure 14:
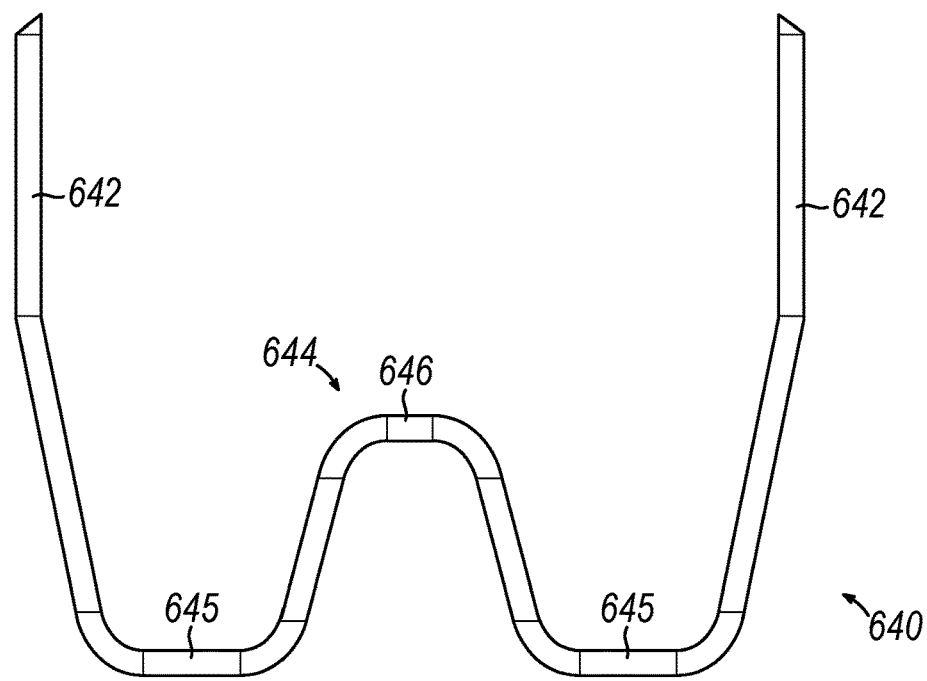
FIG. 14 depicts an elevational front view of an alternative staple that may be applied via the circular stapler of FIG. 1.
Figure 15:
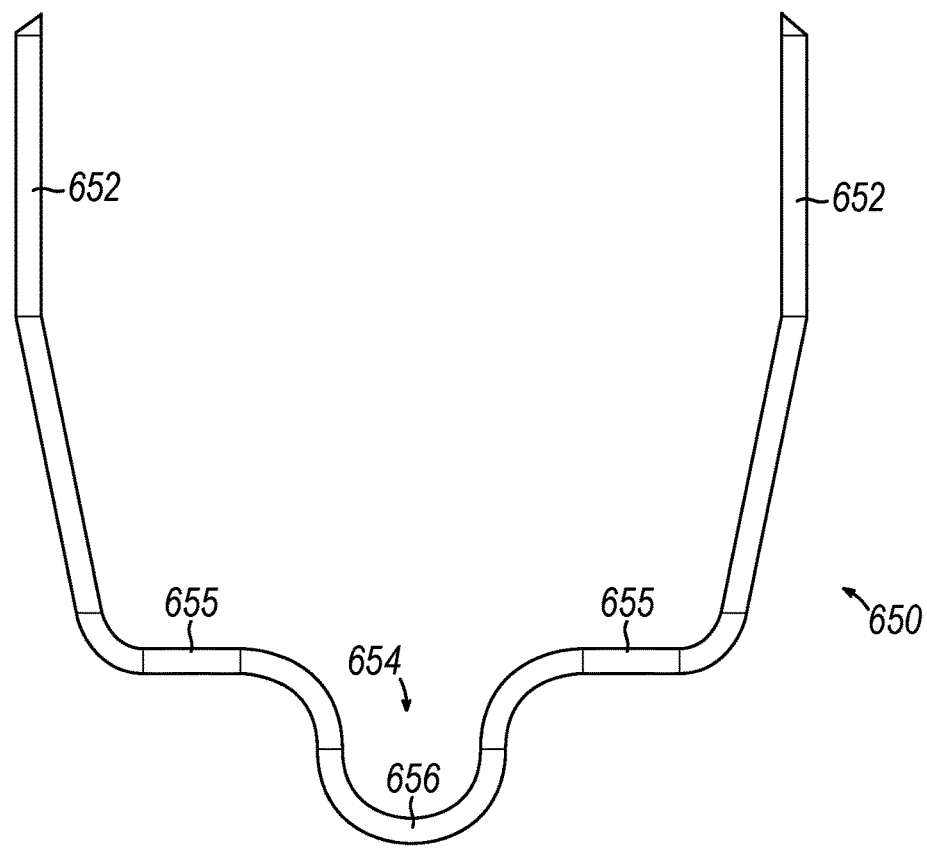
FIG. 15 depicts an elevational front view of an alternative staple that may be applied via the circular stapler of FIG. 1.
Figure 16:
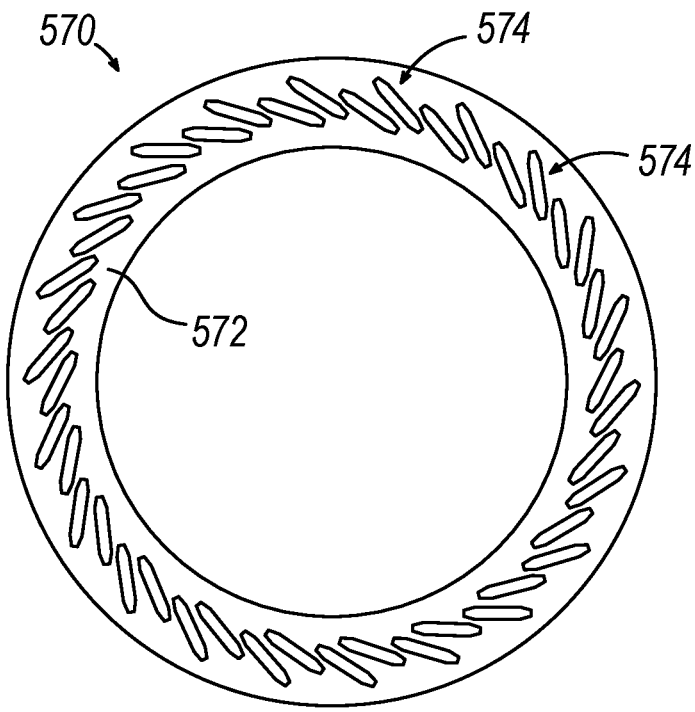
FIG. 16 depicts a top plan view of another alternative deck member that may be incorporated into the stapling head assembly of FIG. 4.
Figure 17:
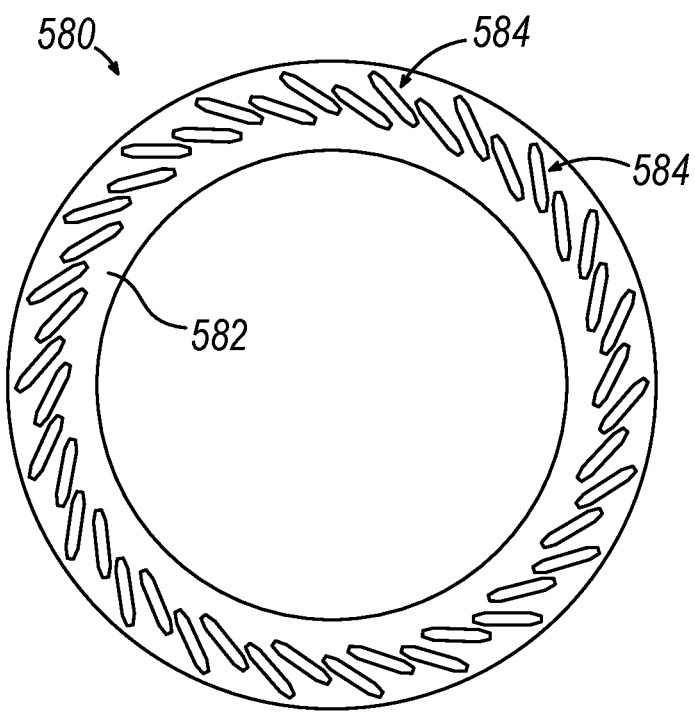
FIG. 17 depicts a top plan view of another alternative deck member that may be incorporated into the stapling head assembly of FIG. 4.
Figure 18:
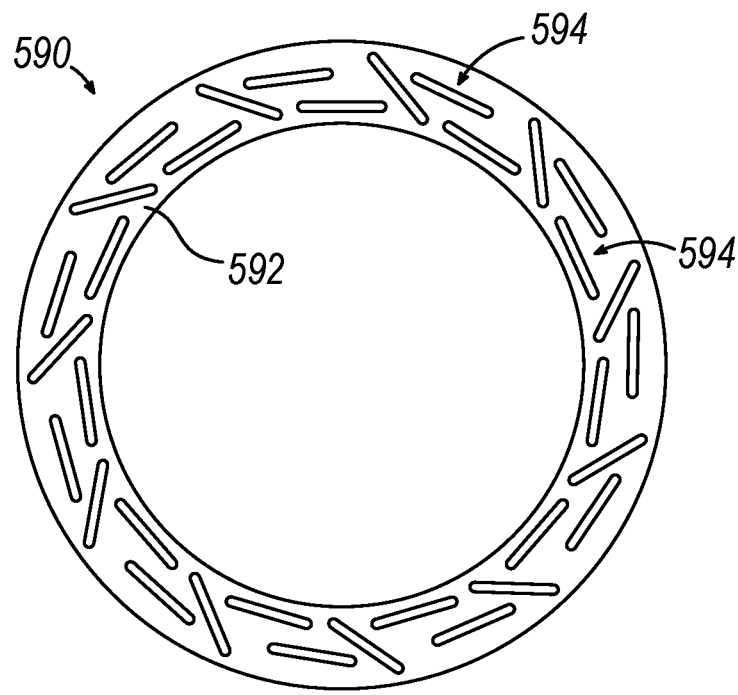
FIG. 18 depicts a top plan view of another alternative deck member that may be incorporated into the stapling head assembly of FIG. 4.
Figure 19:
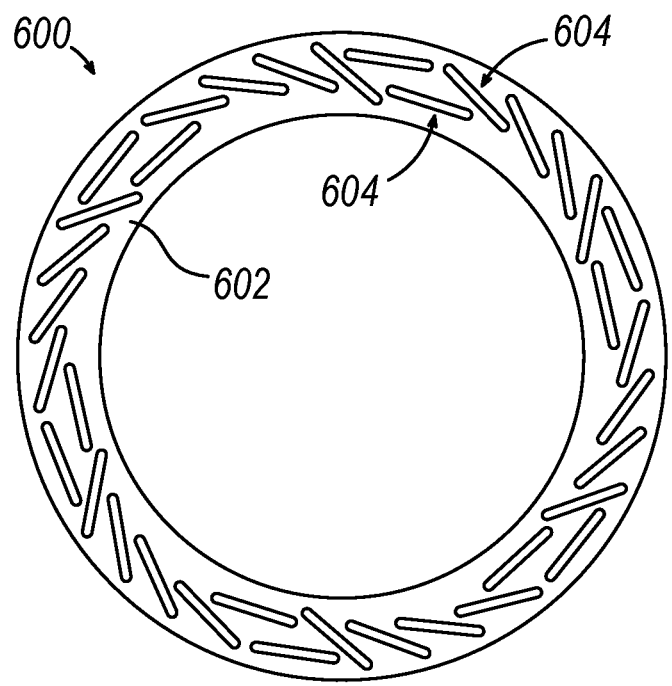
FIG. 19 depicts a top plan view of another alternative deck member that may be incorporated into the stapling head assembly of FIG. 4.
Figure 20:
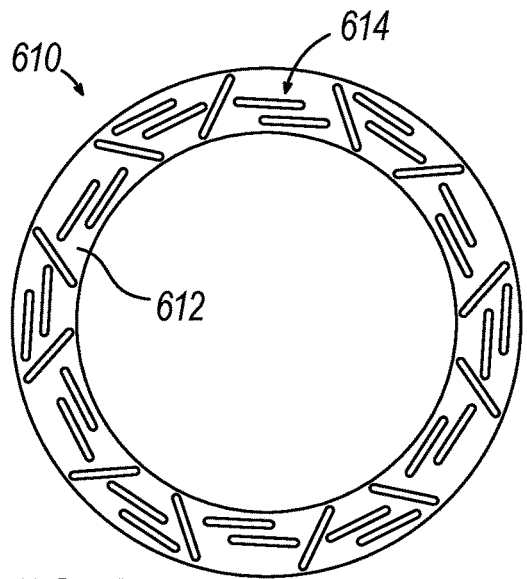
FIG. 20 depicts a top plan view of another alternative deck member that may be incorporated into the stapling head assembly of FIG. 4.
Figure 21:
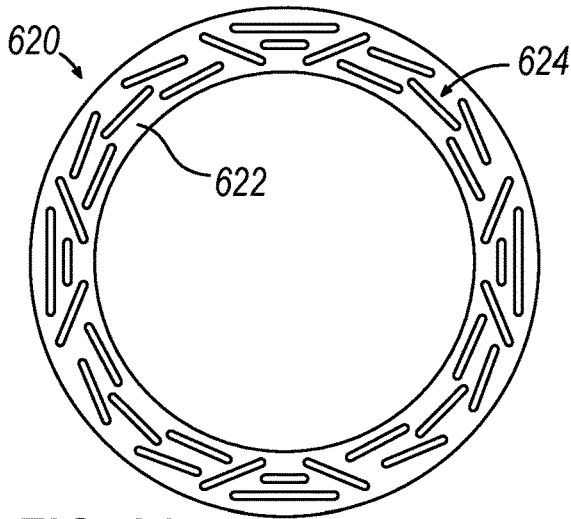
FIG. 21 depicts a top plan view of another alternative deck member that may be incorporated into the stapling head assembly of FIG. 4.
Figure 22:
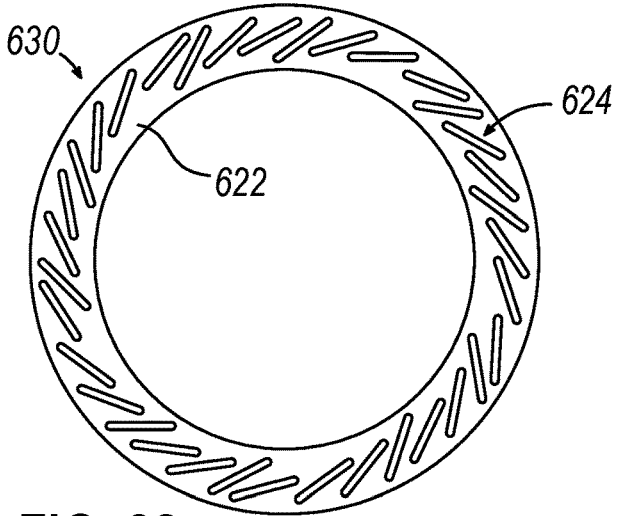
FIG. 22 depicts a top plan view of another alternative deck member that may be incorporated into the stapling head assembly of FIG. 4.

FIGS. 9-13 and 16-22 show a variety of staple decks defining non-tangential staple patterns that do not require increasing the width of their corresponding deck surface. Such staple patterns may in turn enhance the structural integrity of the stapled ends of the anatomical structures (20, 40) to better accommodate expansion and contraction of tubular structures (20, 40). FIGS. 14-15 show a variety of staples (640, 650) that may be incorporated to enhance the structural integrity of staples anatomical structures (20, 40) to better accommodate expansion and contraction of tubular structures (20, 40).

FIG. 9 shows an exemplary staple deck member (510) having a deck surface (512) defined by an outer arched perimeter (e.g., an outer diameter (514)) and an inner arched perimeter (e.g., an inner diameter (516)). Deck surface (512) defines an inner array of staple openings (515), an outer array of staple openings (518), and an intermediate array of staple openings (520) located between the outer and inner arrays of staple openings (515, 518). Staple openings in annular array of staple openings (515, 518, 520) may have any suitable size as would be apparent to one skilled in the art in view of the teachings herein. As an example, staple openings maybe uniform in size and be around 0.03 inches by 0.08 inches in size.

The center of individual staple openings in the inner array of staple openings (515) are position a first distance (d1) away from inner diameter (516). The center of individual staple openings in the intermediate array of staple openings (520) are positioned a second distance (d2) away from inner diameter (516). The center of individual staple openings in the outer array of staple openings (518) are positions a third distance (d3) away from inner diameter (516). As also shown, inner and outer array of staples openings (515, 518) extend along respective axis (522, 524) that are substantially parallel with each other, while intermediate array of staple openings (526) extends along an axis that intersections with axis (522, 524) of inner and outer array of staple openings (515, 518).

Each individual staple extends along a respective axis (522, 524, 526) that is non-tangential with the closest tangent line of the inner and outer diameter (516, 514) of deck surface (512). This is exemplified in FIG. 9 with an individual staple opening of the inner array of staple openings (515) that extends along axis (524) that forms an angle (A1) with its closest tangent line (T1). The closest tangent line for each staple opening (515, 518, 520) may be measured from the center of the respective staple opening (515, 518, 520) as exemplified with distances (d1, d2, d3). With staple openings (515, 518, 520) extending along a non-tangential axis (522, 524, 526) staples fired out of opening may be able to better expand radially after coupling structures (20, 40), thereby enhancing the quality of the anastomosis (70).

In the current example, staple openings in the inner array and out array of staple opening (515, 518) extend along axis (524, 522) that form a 45-degree angle with the closest tangent line, while staple openings in the intermediate array of staple openings (520) extend along an axis (526) that form a 40-degree angle with the closest tangent line. It should be understood that individual staple openings may extend along an axis that forms angles different than other staple openings, even if located in the same array (515, 518).

It should be understood that staple deck member (510) couple with a staple driver member configured to acuate staples housed within openings (515, 518, 520); while an anvil is may have corresponding staple forming pockets dimensioned to deform a corresponding staple driven out of openings (515, 518, 520) in accordance with the description herein. In other words, it should be understood a stapler driver member and an anvil may have complementary features suitably oriented to interact with staples housed within openings (515, 518, 520).

Figure 10:
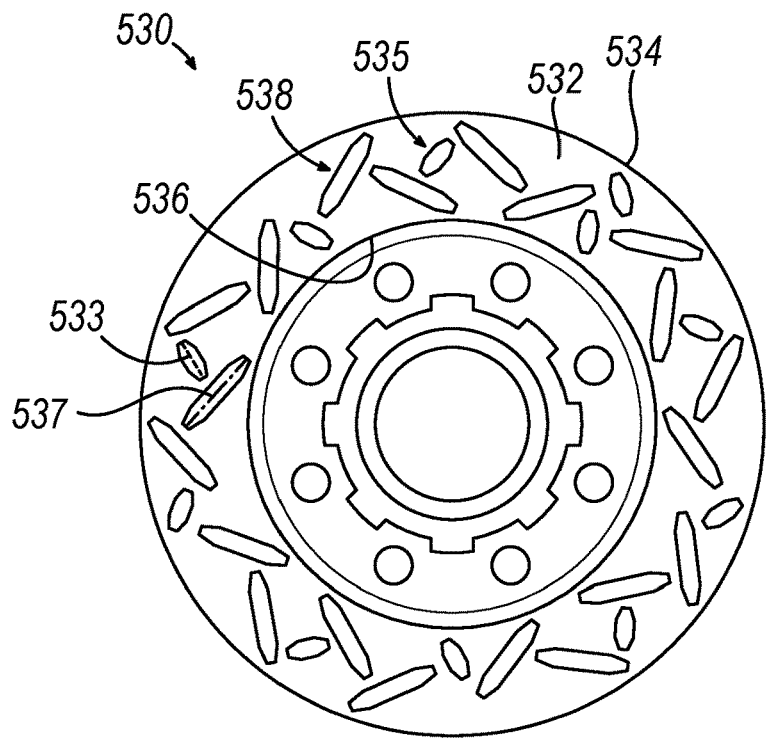
FIG. 10 depicts a top plan view of another alternative deck member that may be incorporated into the stapling head assembly of FIG. 4.

FIG. 10 shows an exemplary staple deck member (530) having a deck surface (532) defined by an outer diameter (534) and an inner diameter (536). In the current example, deck surface (532) defines a plurality of smaller stapler openings (535) and a plurality of larger staples opening (538), all extending non-tangentially on the circumference of deck surface (532). Each large staple opening (538) extends along a respective axis (537) while each small staple opening (535) also extends along a respective axis (533). Similar to axis (522, 524, 526) described above, axis (533, 537) extends to form an angle with the closest tangent line for the individual staple openings (535, 538). With staple openings (535, 538) extending along a non-tangential axis (533, 537), staples fired out of opening may be able to better expand radially after coupling structures (20, 40), thereby enhancing the quality of the anastomosis (70).

Larger staple openings (538) may house larger staples (90), while smaller staple openings (535) may house smaller staples (90). This difference in staple hole sizes may allow for a herringbone pattern to fit within deck surface (532) sized similarly to deck surface (322) describe above. Smaller staples openings (535) may be spread out from each other by having two larger staple openings interposed between adjacent smaller staple openings (535). This may spread the additional stress on stapled tissue caused by using a shorter staple crown in the smaller staples (90).

Figure 11:
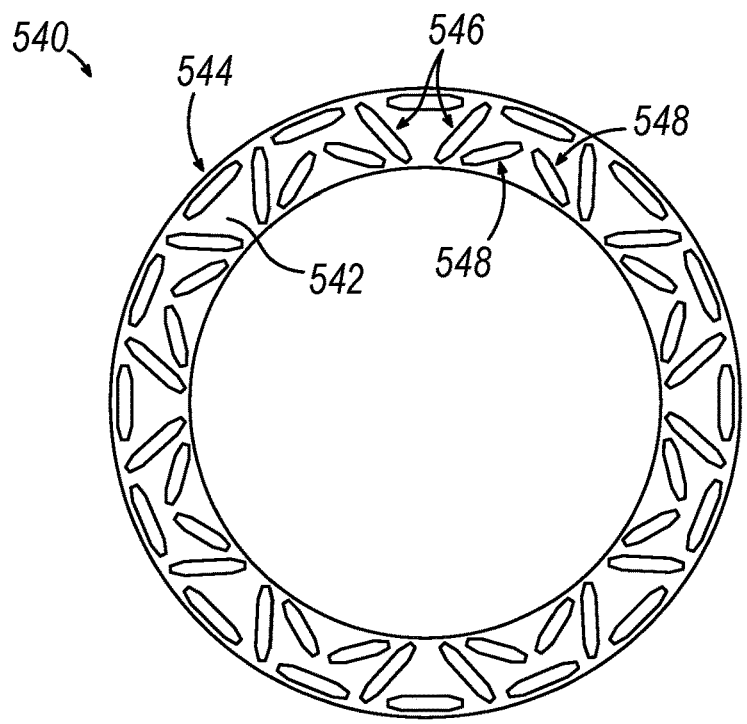
FIG. 11 depicts a top plan view of another alternative deck member that may be incorporated into the stapling head assembly of FIG. 4.

FIG. 11 shows an exemplary staple deck member (540) having a deck surface (542) defined by an outer diameter and an inner diameter. In the current example, deck surface (542) defines an outer array of larger staple openings (544), a plurality of larger oblique staple openings (546), and a plurality of smaller oblique staple openings (546). Outer array of larger staple openings (544) may be tangential, similar to staple openings (324) described above. Oblique staple openings (546, 548) may be non-tangential, similar to stapler openings (535) described above, thereby extending on an axis forming an angle with the closest tangent line for the individual staple openings (546, 548). With staple openings (546, 548) extending along a non-tangential axis, staples fired out of opening may be able to better expand radially after coupling structures (20, 40), thereby enhancing the quality of the anastomosis (70).

This particular pattern of allows for smaller staples in the smaller staple openings (548) to grow in capture length while the longer staples in longer staple openings (544, 546) are able to get closer together allowing for expansion to occur.

Figure 12:
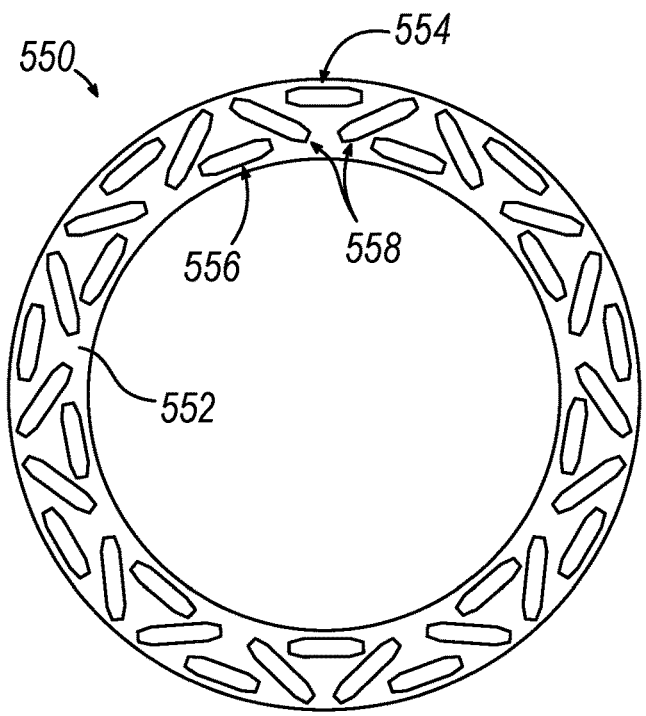
FIG. 12 depicts a top plan view of another alternative deck member that may be incorporated into the stapling head assembly of FIG. 4.

FIG. 12 shows an exemplary staple deck member (550) having a deck surface (552) defined by an outer diameter and an inner diameter. In the current example, deck surface (552) defines an outer array of staple openings (544), an inner array of staple openings (556) and a plurality of oblique staple openings (558). All openings (554, 556, 558) may be substantially the same size. Outer array of staple openings (554) and inner array of staple openings (556) may be tangential, similar to staple openings (324) described above. Oblique staple openings (558) may be non-tangential, similar to staple openings (535) thereby extending on an axis forming an angle with the closest tangent line for the individual staple openings (558). With staple openings (558) extending along a non-tangential axis, staples fired out of opening may be able to better expand radially after coupling structures (20, 40), thereby enhancing the quality of the anastomosis (70). This particular pattern uses on size staple, which may simplify manufacturing.

Figure 13:
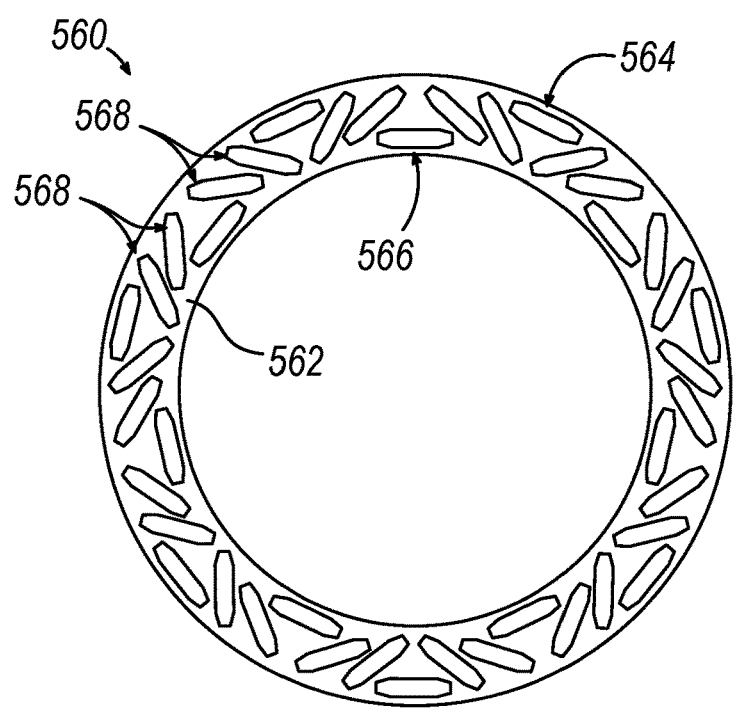
FIG. 13 depicts a top plan view of another alternative deck member that may be incorporated into the stapling head assembly of FIG. 4.

FIG. 13 shows an exemplary staple deck member (560) having a deck surface (562) defining an outer array of staple openings (564), an inner array of staple openings (566) and a plurality of oblique staple openings (568). Staple opening (564, 566, 568) are substantially similar to stapler openings (554, 556, 558) described above, expective that outer and inner array of staple openings (564, 566) are dispersed further apart such that there are fewer outer and inner array of stapling openings (564, 566) and more oblique staple openings (568). This particular pattern may predisposition the fired oblique staples to "lie down" against the fired tangential staples.

FIGS. 16-22 show various other staple deck members (570, 580, 590, 600, 610, 620, 630) having deck surfaces (572, 582, 592, 602, 612, 622, 632) that defines various staple opening (574, 584, 594, 604, 614, 624, 634) forming various staple patterns, either entirely formed of non-tangential staple openings, or some type of combination of non-tangential and tangential staple openings in order to provide the various benefits discussed above.

It should be understood that all staple deck members (510, 530, 540, 550, 560, 570, 580, 590, 600, 610, 620, 630) may couple with a staple driver member configured to acuate staples housed within openings (515, 518, 520, 535, 538, 544, 546, 548, 554, 556, 558, 564, 566, 568, 574, 584, 594, 604, 614, 624, 634); while an anvil may have corresponding staple forming pockets dimensioned to deform a corresponding staple driven out of openings (515, 518, 520, 535, 538, 544, 546, 548, 554, 556, 558, 564, 566, 568, 574, 584, 594, 604, 614, 624, 634) in accordance with the description herein. In other words, it should be understood a stapler driver member and an anvil may have complementary features suitably oriented to interact with staples housed within openings (515, 518, 520, 535, 538, 544, 546, 548, 554, 556, 558, 564, 566, 568, 574, 584, 594, 604, 614, 624, 634).

As mentioned above, FIGS. 14-15 show different staples (640, 650) that may be readily incorporated into any staple deck member (320, 510, 530, 540, 550, 560, 570, 580, 590, 600, 610, 620, 630) described above in order to enhance the structural integrity of stapled anatomical structures (20, 40) by promoting expansion of staples (640, 650) in response to being under tension, such as when tubular structures (20, 40) expand during peristalsis.

First staple (640) includes a pair of legs (642) connected together by a crown (644). Legs (642) may be substantially similar to legs of staples (90) described above. Therefore legs (642) may bend in response to contact with staple forming pockets (414) of anvil in order to staple anatomical structure (20, 40) together. Crown (644) includes a pair a lateral connecting members (654) extending from an end of a respective leg (642) toward each other. Both lateral connecting members (645) extend into an upward bend (646).

Upward bend (646) may allow for a fired stapled (640) to provide a higher compression of stapled tissue, which may enhance the quality of an anastomosis (70). Additionally, upward bend (646) may provide additional material for cross (644) to expand under tension, thereby acting a spring. In other words, that additional material provided by upward ben (646) may allow crown (644) to expand when staple (640) is under a tension that pulls lateral conniving members (645) away from each other. Therefore, when staple (640) is fired in a non-tangential relationship, radial expansion of anatomical structures (20, 40) may pull crown (644), at least partially in a direction that promotes such expansion of crown (644).

Second staple (650) includes a pair of legs (652) connected together by a crown (654). Legs (652) may be substantially similar to legs of staples (90) described above. Therefore legs (652) may bend in response to contact with staple forming pockets (414) of anvil in order to staple anatomical structure (20, 40) together. Crown (654) includes a pair a lateral connecting members (655) extending from an end of a respective leg (652) toward each other. Both lateral connecting members (655) extend into a downward bend (656).

Downward bend (656) may provide similar spring like characteristics as to upward bend (646) described above. Additionally, downward bend (656) extends away from legs (652), thereby proving room such that tips of legs (652) may not contact crown (654) as legs (652) bend toward crown (654). This may inhibit crown (654) from developing any surface irregularities after the firing of staple (650) due to contact with sharp portions of legs (652), which may in turn prevent crown (654) from developing any sharp surfaces caused by such contact.

B. Exemplary Firing Member Increasing the Diameter of Knife Member

Figure 23:
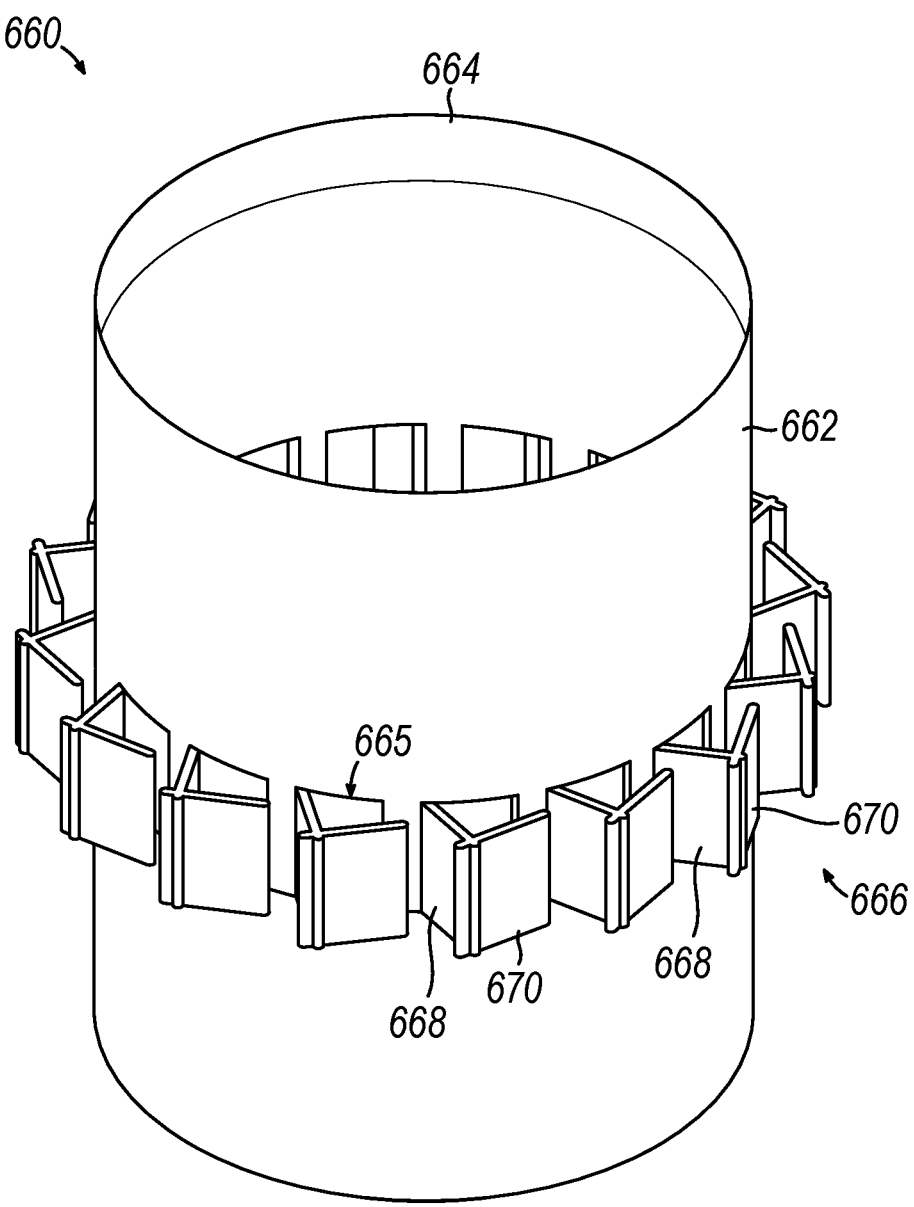
FIG. 23 depicts a perspective view of an exemplary firing member that may be readily incorporated into the stapling head assembly of FIG. 4.

In some instances, it may be desirable to increase the diameter of knife number (340) in order to reduce the length at which anastomosis (70) and severed edges (60) extend radially inward from the interior of the tubular anatomical structure (20, 40). FIG. 23 shows an example firing number (660) that may readily incorporated into stapling head assembly (300) describe above. In particular, firing member (660) includes a cylindraceous body (662) terminating distally into a cutting edge (664). Cutting edge (664) may act similar to cutting edge (342) described above. Cylindraceous body (662) may be actuated in similar fashion to that of staple driver member (350) and knife member (340) described above.

Additionally, firing member (660) includes a plurality of staple drives (666) fixed to and extending radially outward from cylindraceous body (662). In the current example, staple drivers (666) extend away from a portion of cylindraceous body (662) defining an opening (665). Staple drivers (666) each include a first firing body (668) directly fixed to cylindraceous body (662) and a second firing body (670) extending from first firing body (668). Each firing body (668, 670) may be configured to drive an individual staple (90, 640, 650) such that one staple driver (666) may fire two or more staples (60, 640, 650) aligned in a non-tangential relationship similar to the non-tangential relationship described above.

Figure 24:
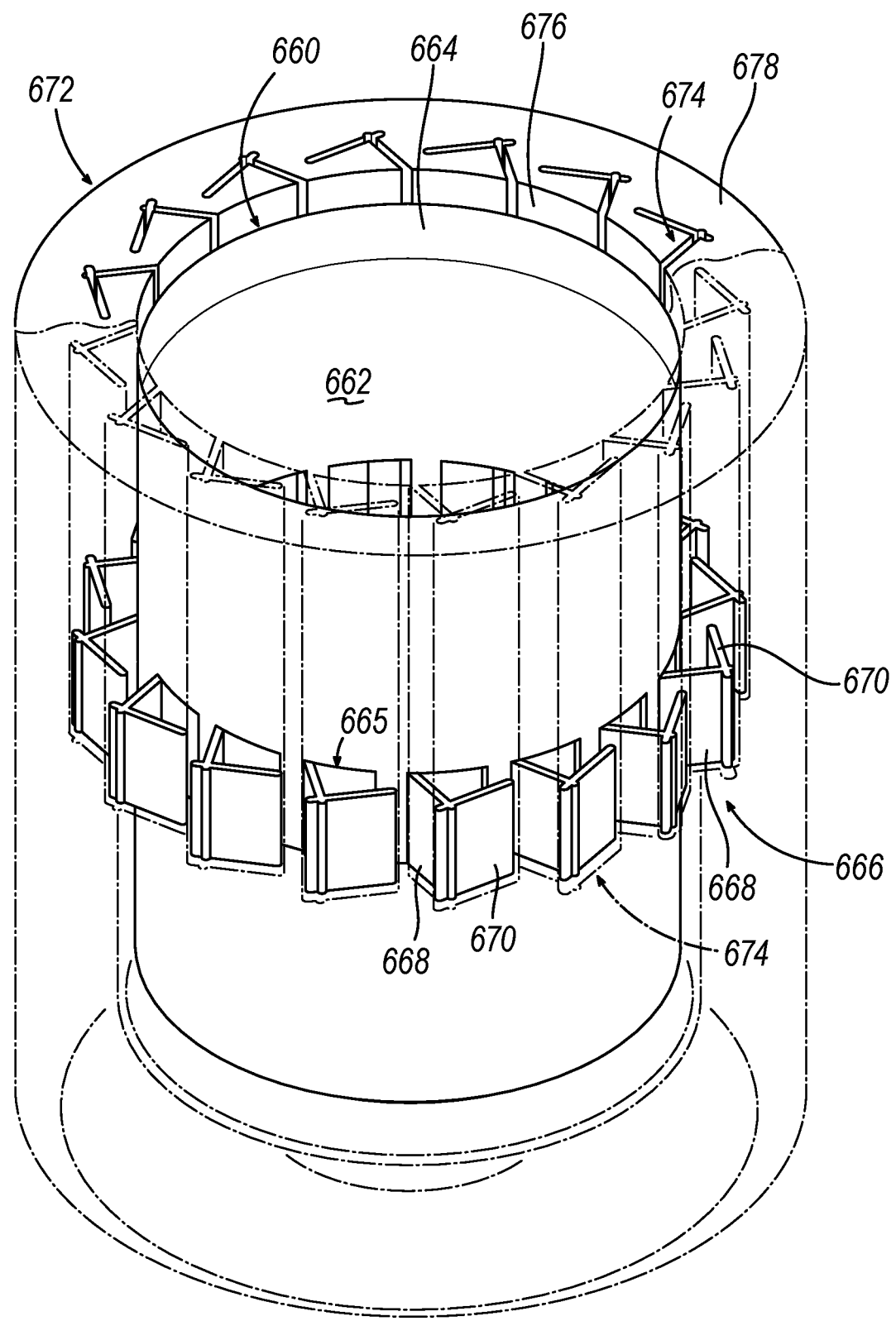
FIG. 24 depicts a perspective view of the firing member of FIG. 23 slidably contained in an exemplary tubular body member and staple deck that may be readily incorporated into the stapling head assembly of FIG. 4.
Figure 25:
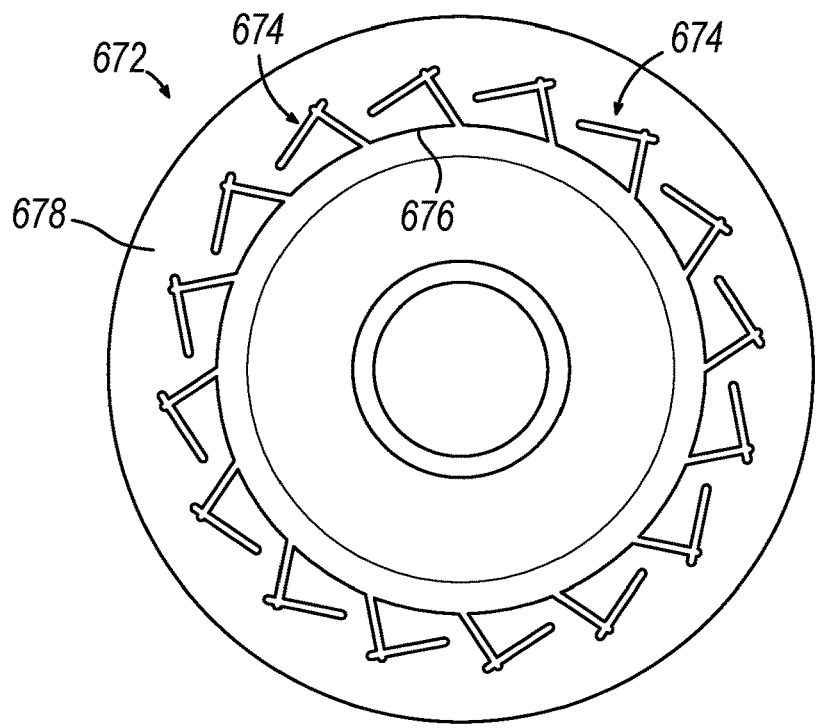
FIG. 25 depicts a top plan view of the firing member of FIG. 23 and the staple deck of FIG. 24.

As will be described in greater detail below, since staple drives (666) and cutting edge (664) are incorporated into a single firing member (660), cutting edge (664) may have a larger diameter (664) compared to cutting edge (342) described above. FIG. 24 shows firing member (660) slidably housed within a tubular body member (672), while FIG. 25 shows tubular body member (672). Tubular body number (672) may be readily incorporated into stapling head assembly (300) described above in replacement of tubular body member (310) described above. It should be understood that tubular body member (672) may include a core member similar to core member (312) described above.

Tubular body member (672) includes an interior surface (676) defining a recessed cavity which slidably houses cylindraceous body (662). Cylindraceous body (662) may slidingly abut against interior surface (676), which in turn may allow for cutting edge (664) to be larger in diameter compared to cutting edge (342) described above. Tubular body number (672) also includes a top surface (678). Top surface (678) may act as a deck surface, similar to deck surface (322) described above. Alternatively, top surface (678) may be configured to attach to a suitable deck surface. Top surface (678) and interior surface (676) together define a plurality of complementary driver recesses (674) dimensioned to slidably house a corresponding staple driver (666). Driver recesses (674) may also contain staples (90, 640, 650), which may rest above a respective driving body (668, 670) such that actuation of driving body (668, 670) toward top surface (678) drives staples (90, 640, 650) distally past top surface (678).

Due to this configuration of tubular body member (672) and firing member (660), fired staples (90, 640, 650) may be radially closer to cutting edge (664) as compared to stapling head assembly (300) described above. Therefore, utilizing tubular body member (672) and firing member (660) may allow an operator to fire staples (90, 640, 650) in a non-tangential relationship while also reducing the size at which severed edges (60) extend from the interior of lumens (20, 40).

Figure 26:
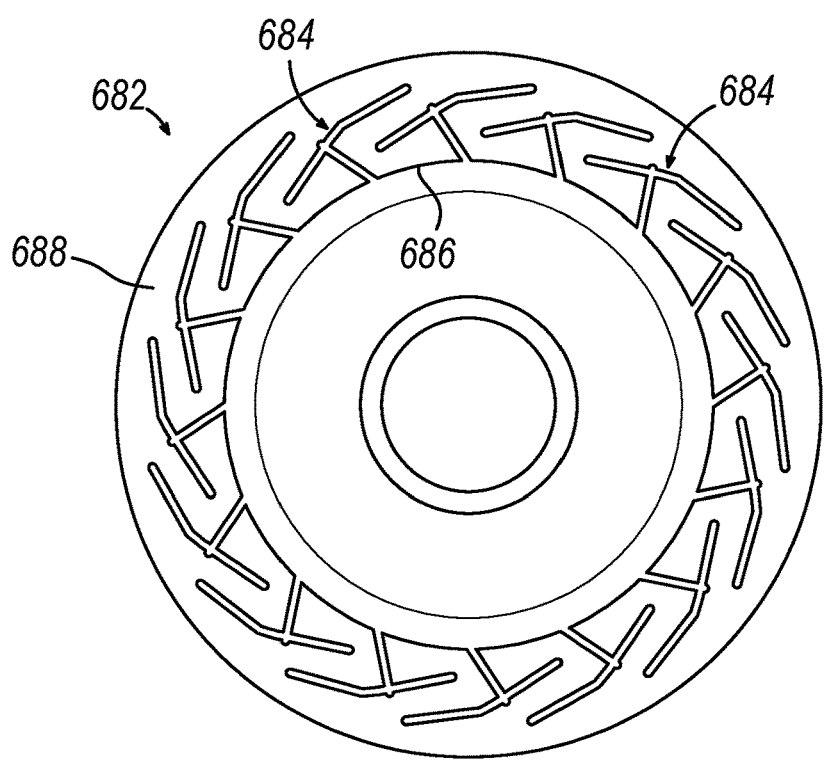
FIG. 26 depicts a top plan view an alternative firing member and staple deck that may be readily incorporated into the stapling head assembly of FIG. 4.
Figure 29:
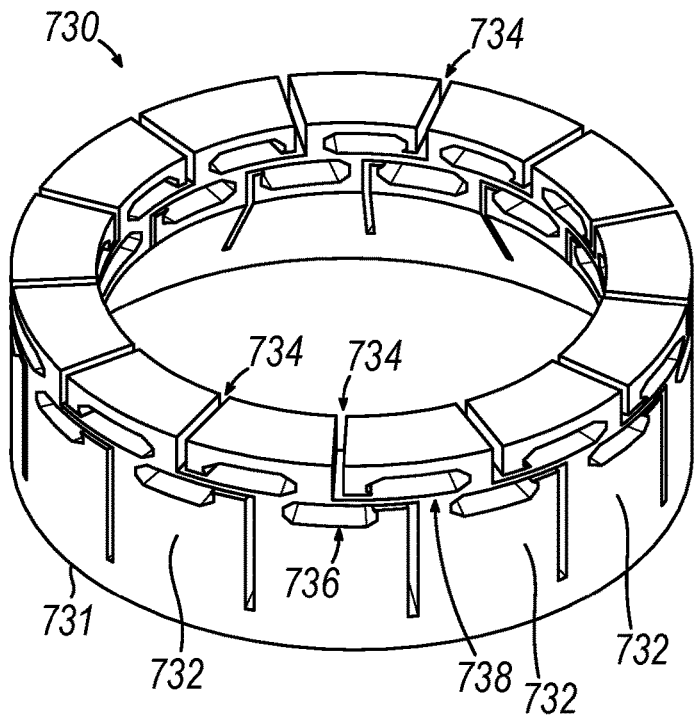
FIG. 29 depicts a perspective view of an alternative deck assembly that may be incorporated into the stapling head assembly of FIG. 4, the deck assembly being configured to capture tissue for stapling in a radial direction.

While staples drivers (666) currently include a first driving body (668) and a second driving body (670) configured to each fire a staple (90, 640, 650), staple drivers (666) may be configured with more driving bodies such that staple drivers (666) may fire more staples. FIG. 26 shows an alternative tubular body member (682) that is substantially similar to tubular body member (672) described above, with differences elaborated below.

Therefore, tubular body member (682) includes an interior surface (686), a top surface (688), and a plurality of complementary driver recesses (684). Tubular body member (684) is configured to receive a staple driver that may fire three staples (90, 640, 650) rather than two. Tubular body member (682) is substantially similar to tubular body member (672) described above, except complementary driver recess (684) is modified to receive a staple driver with three driver bodies, thereby allowing tubular body member (682) to house staples (90, 640, 650) oriented in a different staple pattern. Therefore, it should be understood, firing member (660) and tubular body member (672) may be modified to fire any suitable staple pattern as would be apparent to one skilled in the art in view of the teachings herein.

C. Exemplary Stapling Head Assemblies Reducing the Width of Staple Deck

In some instances, it may be desirable to fire staples in a radial direction (either partially or entirely) of stapling head assembly (300) rather than in the longitudinal direction of stapling head assembly (300). This may allow for staples to covers a greater surface area of stapled tissue (20, 40), thereby enhancing the staple quality, without having to increase the amount of space severed ends (60) takes up within the anatomical structures (20, 40).

FIGS. 27-28B show an anvil (700) and a stapling head assembly (706) that may be used to fire staples (90) in a direction that has a radial axis (R) and a longitudinal axis (LA) component rather than strictly just a longitudinal axis (LA) component. Anvil (700) is substantially similar to anvil (400) described above, but with difference elaborated below. In particular, anvil (700) includes an obliquely oriented proximal stapling surface (702) defining a plurality of staple forming pockets (704). Compared to proximal stapling surface (412) of anvil (400) described above, obliquely oriented proximal stapling surface (702) faces a normal direction that has at least a component in the radial direction defined by radial axis (R). As will be described in greater detail below, this radial direction component may allow anvil (700) to capture and staple a greater surface area of tissue (20, 40) without producing severed ends (60) that extend further within lumens (20, 40) in the radial direction.

Stapling head assembly (706) may be substantially similar to stapling head assembly (300) described above, but with differences described below. In particular, stapling head assembly (706) includes an obliquely oriented deck surface (708) defining staple opening (710), a longitudinal driver (710), and a plurality of oblique staple drivers (714) slidably housed within a respective staple opening (710). Obliquely oriented deck surface (708) faces in a normal direction that extends in a complementary fashion with deck surface (708) such that as anvil (700) is proximally driven in order to grasp tissue (20, 40), tissue (20, 40) located between surfaces (702, 708) may be suitably stapled in accordance with the description herein. Therefore, as best seen between FIGS. 28A-28B, anvil (700) may be proximally actuated toward stapling head assembly (706) such that tissue (20, 40) may be grasped between surfaces (702, 708) while surfaces (702, 708) define a suitable gap distance.

Staple openings (710) may together form any suitable staple pattern as would be apparent to one skilled in the art in view of the teachings herein. Staple openings (710) are dimensioned to slidably house an oblique driver (715) and a corresponding staple (90) such that oblique driver (715) may actuate along a path that is substantially parallel with the normal direction of deck surface (708). Longitudinal driver (712) is configured to actuate along a path parallel with longitudinal axis (LA). However, as also exemplified between FIGS. 28A-28B, longitudinal driver (712) is configured to abut against oblique driver (714) such that actuation of longitudinal driver (712) driver movement of oblique driver (714) toward deck surfaced (708) to thereby drive staple (90) against staple forming pocket (704) to suitable staple tissue (20, 40) in accordance with the description herein.

Figure 44:
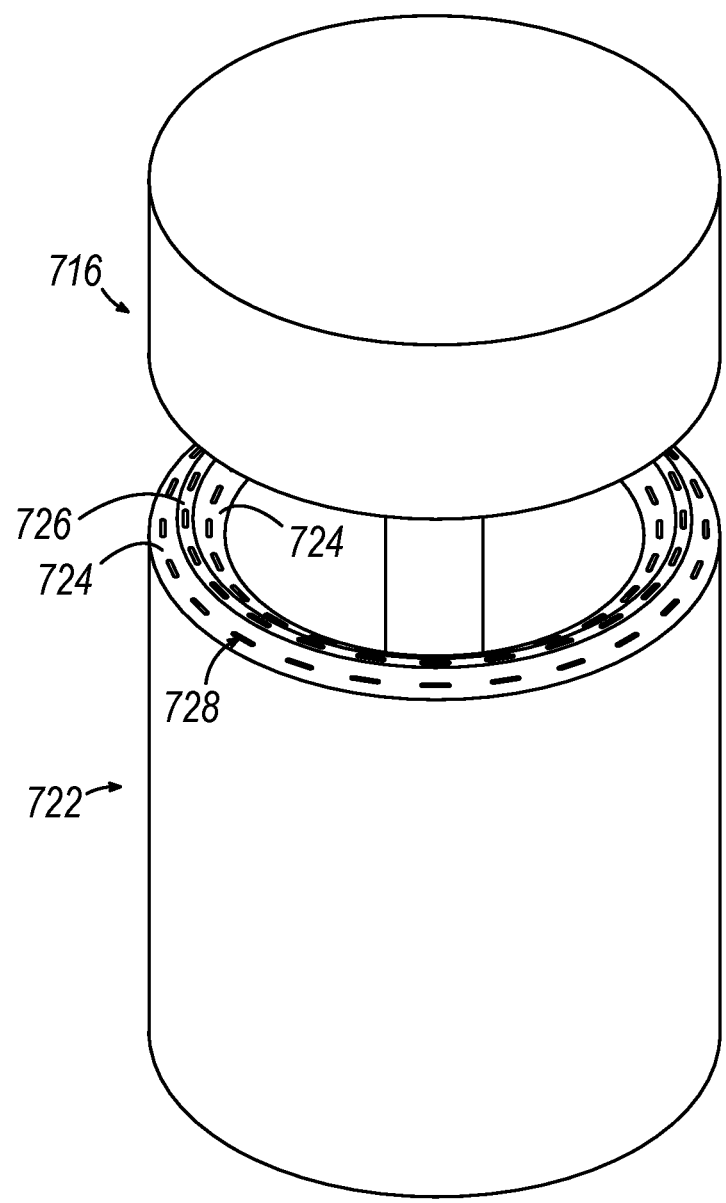
FIG. 44 depicts a perspective view of an alternative anvil and stapling head assembly that may be incorporated into the circular stapler of FIG. 1.
Figure 45:
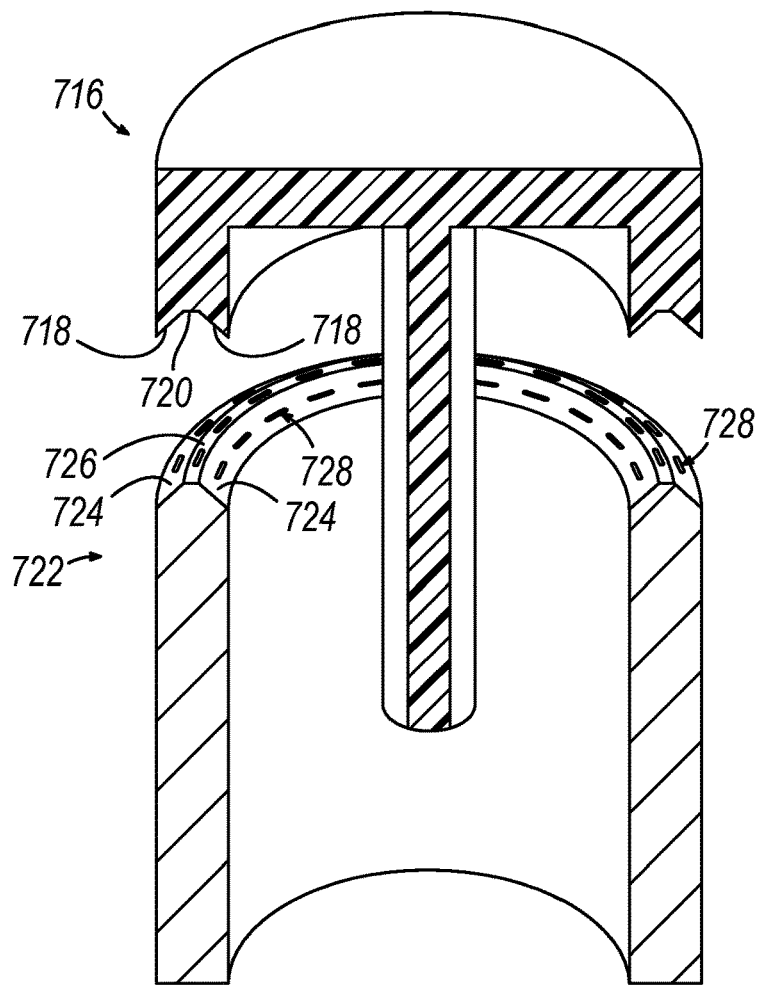
FIG. 45 depicts a cross-sectional view of the anvil and stapling head assembly of FIG. 44.
Figure 46:
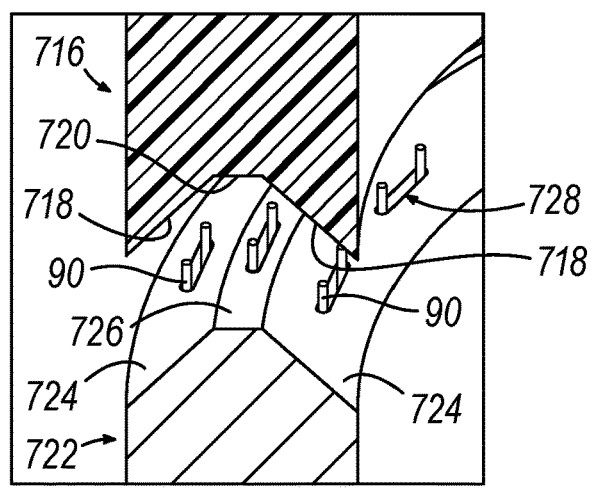
FIG. 46 depicts an enlarged perspective view of the anvil and stapling head assembly of FIG. 44.

In some instances, it may be desirable to utilize oblique surfaces (702, 708) to grasp tissue (20, 40), but still fire staples (90) in a longitudinal direction. Grasping tissue (20, 40) with oblique surface (702, 708) may increase the surface area interaction with tissue (20, 40) and also may reduce tissue strain on stapled tissue. FIGS. 44-46 show an exemplary anvil (716) and stapling head assembly (722) that may be substantially similar to anvil (400) and stapling head assembly (300) described above, but with differences elaborate below. In particular, anvil (716) includes a pair of obliquely oriented proximal surfaces (718) connected by a flat proximal surface (720), while stapling head assembly (722) includes a pair of obliquely oriented deck surfaces (724) connected by a flat deck surface (726). Each surface (724, 726) defining an annular row of staple openings (728) while each surface (718, 720) includes complementary staple forming pockets.

Surfaces (718, 720) on anvil (716) are complementary to surfaces (724, 726) on stapling head assembly (722) such that when tissue (20, 40) is captured, a suitable gap distance may be defined. Grasping tissue (20, 40) with oblique surfaces (718, 724) and flat surfaces (720, 726) may increase the surface area interaction with tissue (20, 40) and also may reduce tissue strain on stapled tissue. As shown in FIG. 46, staples (90) may be fired longitudinally out of openings (728).

In instances where staples (90) are fired in the radial direction, tissue (20, 40) may also need to be compressed in the radial direction to form a suitable gap distance (d). Proximal retraction of anvil (400) to form gap distance (d), as discussed above, may not provide the necessary compression required to form gap distance (d) for firing staples (90) in the radial direction. FIGS. 29-30A and FIGS. 31-33B show two different examples of a staple deck assembly (730, 745) that may be used to form a gap distance (d) in the radial direction.

As shown in FIGS. 23-30A, staple deck assembly (730) includes an annular base (731) acting as a connecting point for an annular array of resilient bodies (732). Annular array of resilient bodies (732) each define a lower staple opening (736) and an upper staple opening (738) such that resilient bodies (732) as a whole together define an upper array of staple openings and a lower array of staple openings. Resilient bodies (732) are separated from adjacent resilient bodies (732) via a respective cut-out (734), thereby allowing resilient bodies (732) to radially flex relative to annular base (731). Resilient bodies (732) may radially flex relative to annular base (731) in order to compress tissue (20, 40) between radially facing surface (744) of an anvil (742) in order to define a suitable gap distance (d).

Figure 30A:
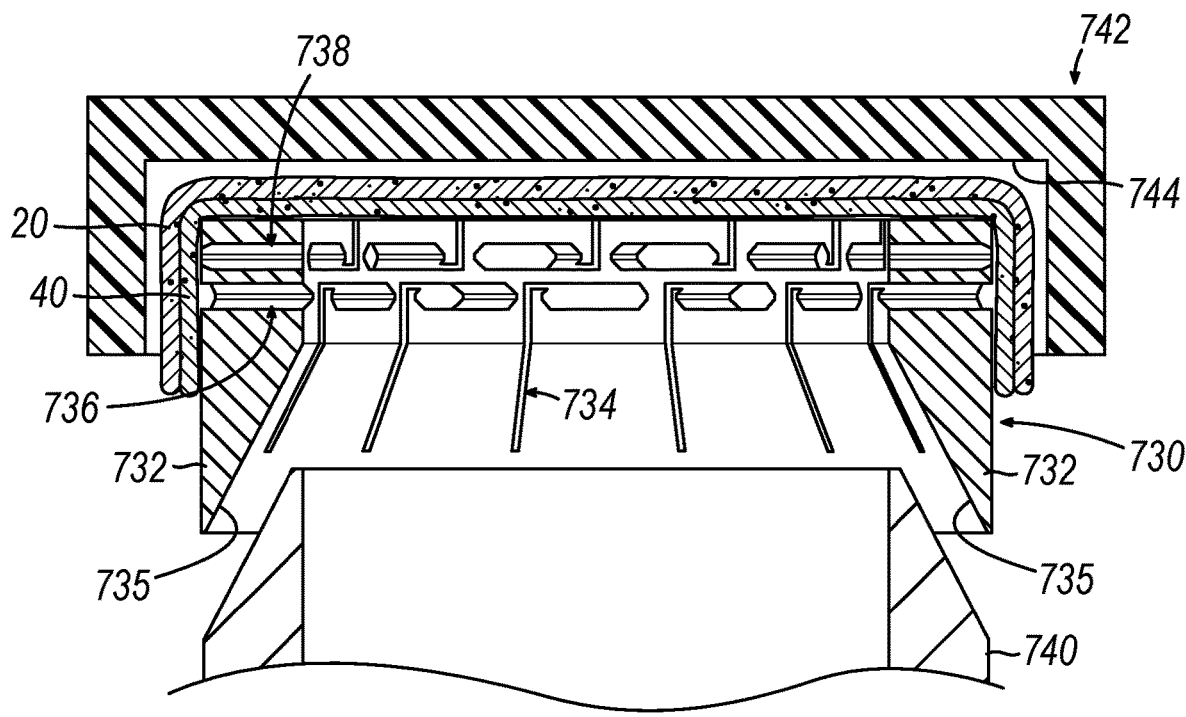
FIG. 30A depicts a cross-sectional view of the deck assembly of FIG. 29 capturing tissue with an anvil.
Figure 30B:
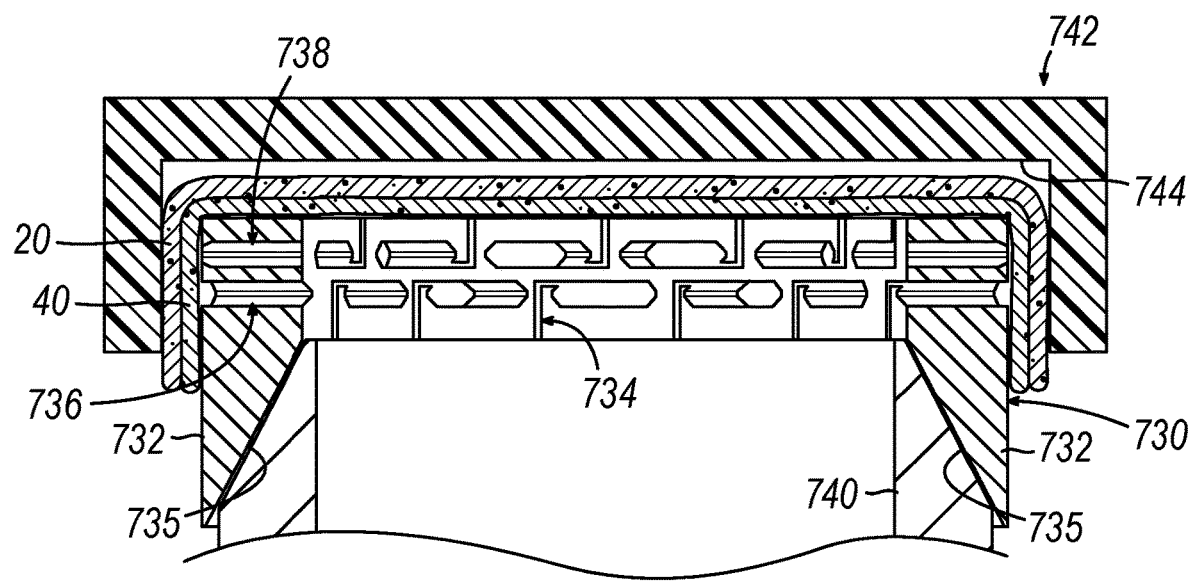
FIG. 30B depicts a cross-sectional view of the deck assembly of FIG. 29 further capturing tissue with an anvil.
Figure 31:
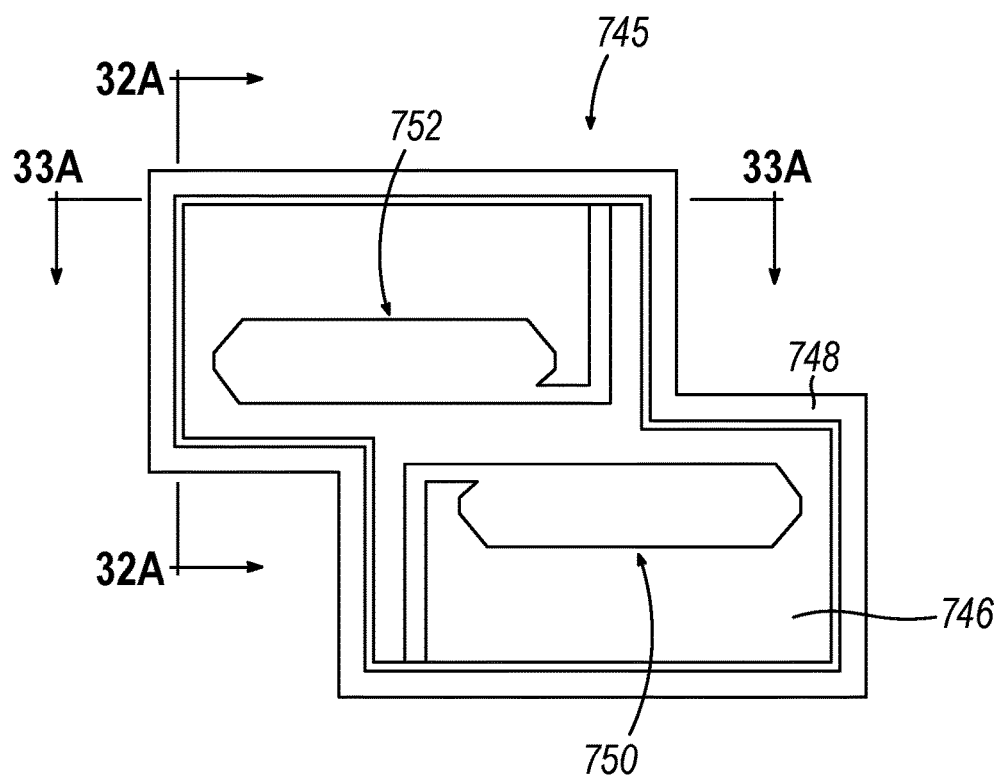
FIG. 31 depicts a front elevational view of another alternative deck assembly that may be incorporated into the stapling head assembly of FIG. 4, the deck assembly being configured to capture tissue for stapling in a radial direction.
Figure 32A:
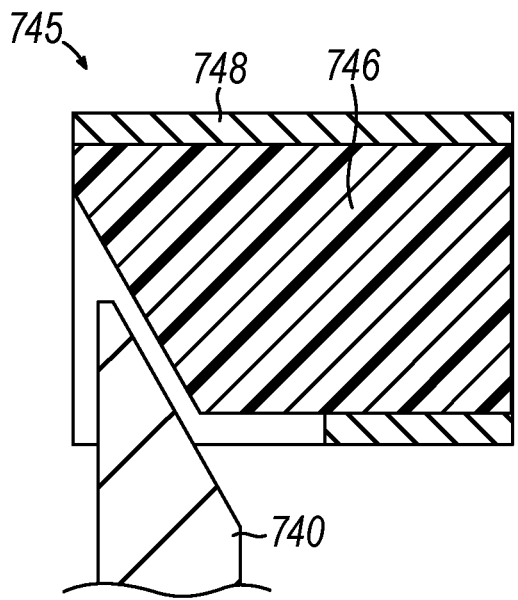
FIG. 32A depicts a cross-sectional view of the deck assembly of FIG. 31, taken along line 32A-32A of FIG. 31, where the deck assembly is in a first position.
Figure 32B:
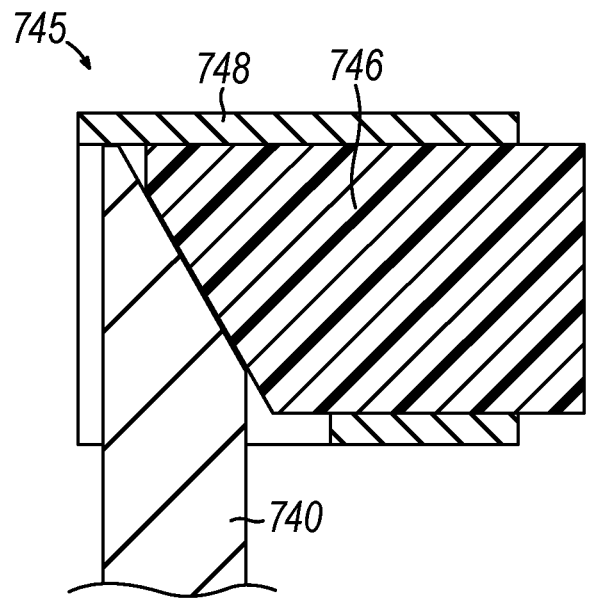
FIG. 32B depicts a cross-sectional view of the deck assembly of FIG. 31, taken along line 32A-32A of FIG. 31, where the deck assembly is in a second position.
Figure 33A:
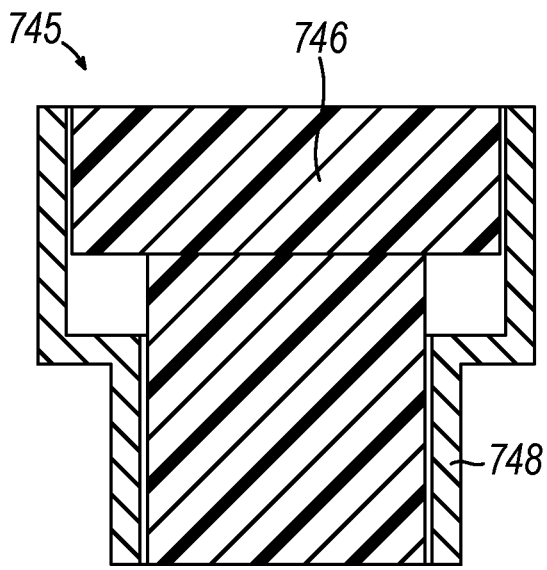
FIG. 33A depicts a cross-sectional view of the deck assembly of FIG. 31, taken along line 33A-33A of FIG. 31, where the deck assembly is in the first position.
Figure 33B:
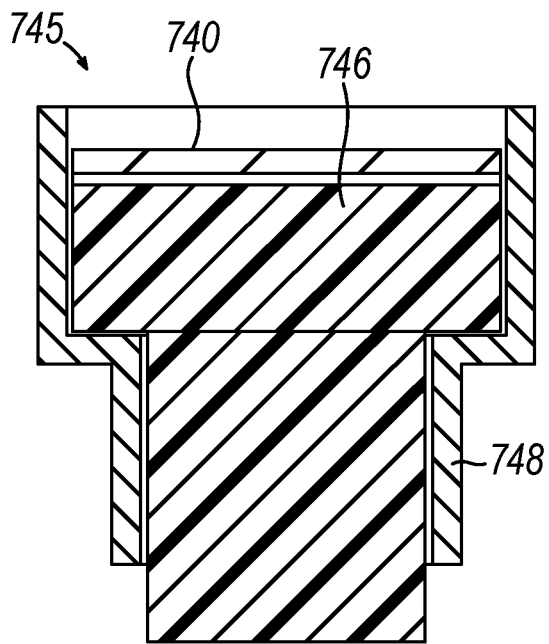
FIG. 33B depicts a cross-sectional view of the deck assembly of FIG. 31, taken along line 33A-33A of FIG. 31, where the deck assembly is in the second position.
Figure 34:
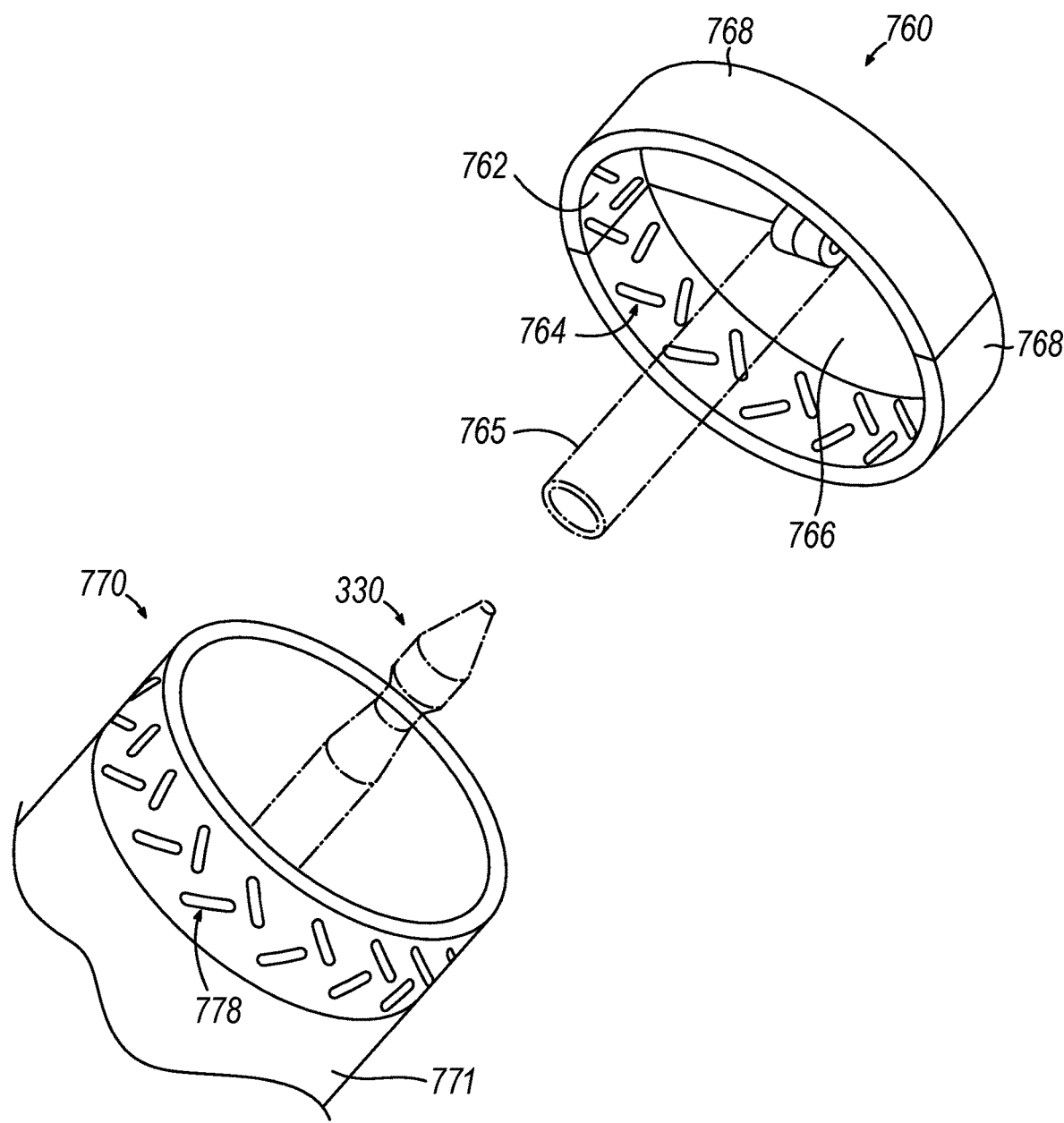
FIG. 34 depicts a perspective view of an alternative anvil and stapling head assembly that may be incorporated into the circular stapler of FIG. 1.

As best shown in FIGS. 30A-30B, each resilient body (732) includes a tapered cam surface (735). Tapered cam surface (735) may engage a longitudinally actuating cam body (740). In particular, as longitudinally actuating cam body (740) actuates distally in the longitudinal direction, contact between cam body (740) and cam surface (735) drives resilient bodies (732) toward radially facing surface (744) of anvil (740). Resilient bodies (732) are sufficiently resilient such that if cam body (740) is driven proximally, resilient bodies (732) may then flex radially inward. Therefore, it should be understood that an operator may control the gap distance (d) between resilient bodies (732) and radially facing surface (744) of anvil (742) by actuating longitudinally translating cam body (740) distally and proximally.

Anvil (742) may be substantially similar to anvil (400) described above, with differences elaborated below. Radially facing surface (744) may have suitable staple forming pockets aligned with staples openings (736, 738). Staple openings (736, 738) may house an individual staple (90) such that staples may be fired radially outward from staple opening (736, 738) against staple forming pockets of radially facing surface (744) in order to staple tissue (20, 40) captured between resilient bodies (732) and radially facing surface (744).

In some instances, rather than flex resilient bodies (732) toward and away an annular base (731), it may be desirable to translate bodies defining staple openings (736, 738) within a housing in order to define gap distance (d) in the radial direction in accordance with the description herein. FIGS. 31-33B show a segment of an exemplary deck assembly (745). Deck assembly (745) includes a plurality of radially translating bodies (746) which may be slidably contained in a housing (748). Housing (748) may extend in an annular shape while slidable containing individual bodies (746). Bodies (746) may define staple openings (750, 752), such that when bodies (746) are assembled as a whole within housing (748), staple openings (750, 752) form an upper and lower array of stapler openings in a similar shape formed by style openings (736, 738) described above.

As shown in FIGS. 32A-33B, in order to control the gap distance (d) in this example, translating cam body (740) may engage a portion of translating bodies (746) to thereby push translating bodies (746) along a radial path defined by housing (748), thereby allowing an operator to determine and set a desired gap distance (d) in accordance with the description herein. Translating bodies (746) may be sufficiently resilient such that if translating cam body (740) disengages bodies (746), bodies (746) may return to the position shown in FIGS. 32A and 33A.

FIGS. 34-36C show an exemplary anvil (760) and stapling head assembly (770) that may be used to fire a plurality of staples (90) in the radial direction while also severing tissue (20, 40) captured between anvil (760) and stapling head assembly (770). Anvil (760) includes a pair of coupling halves (768) pivotally attached to each other via a pin (769), and a shank (765) extending away from coupling halves (768). Shank (765) may be substantially similar to shank (420) described above. Therefore, shank (765) may be configured to couple to trocar (330) in order to actuate anvil (760) proximally toward stapling head assembly (770) in accordance with the description herein.

Figure 35A:
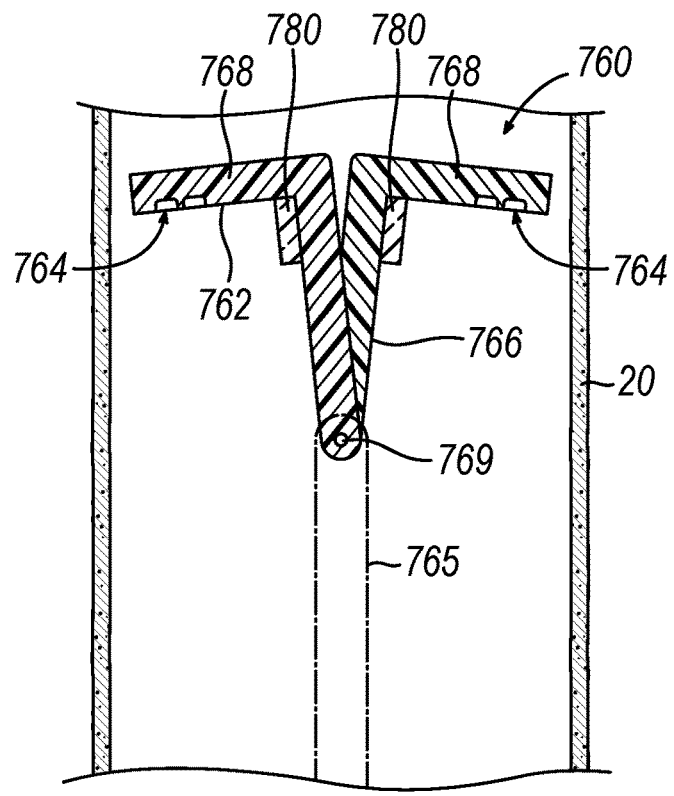
FIG. 35A depicts a cross-sectional view of the anvil of FIG. 34 in a folded position being inserted within a lumen of a patient.
Figure 35B:
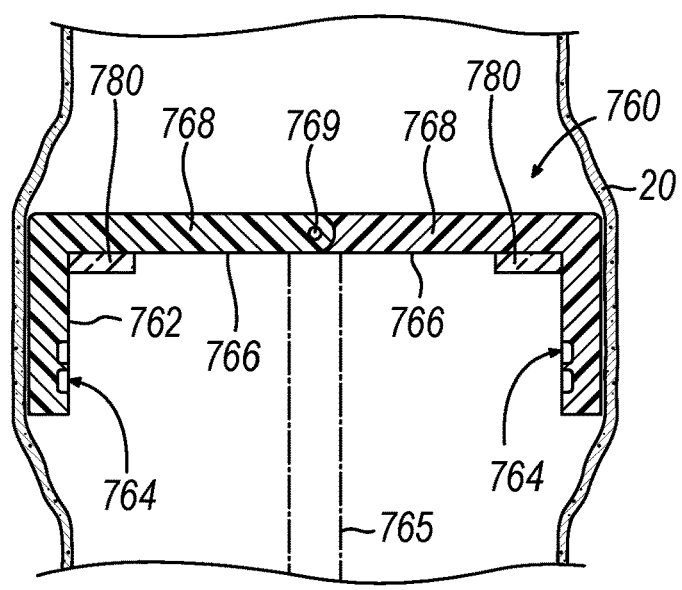
FIG. 35B depicts a cross-sectional view of the anvil of FIG. 34 in an unfolded position within the lumen of a patient.

Coupling halves (768) fold about pin (769) between a folded position (see FIG. 35A) and an unfolded position (see FIG. 35B). In the folded position, anvil (760) may more easily be inserted through an anatomical structure (20) for purposes of placing anvil (760) near stapling head assembly (770). In the unfolded position, coupling halves (768) together form a radially facing surface (762) defining staple forming pockets (764) and a flat surface (766). Staple forming pockets (764) may align with staples (90) during firing of staples (90) in accordance with the description herein, while flat surface (766) may be configured to cooperate with a cutting edge (776) of stapling head assembly (770) in order to sever tissue (20, 40).

Stapling head assembly (770) includes a cylindraceous body (771) defining a plurality of radially facing staple openings (778), a cylindrical firing member (772) slidably disposed within cylindraceous body (771), and a plurality of radially actuating staple drivers (775) each suitably attached to a staple (90) aligned with a respective staple opening (778). Firing member (772) includes a camming surface (774) and a distally presented cutting edge (776). Camming surface (774) is configured to actuate distally in order to drive stapler drivers (775) radially out toward staple openings (778) such that staples (90) are driven into staple forming pockets (764) of anvil (760) in order to staple tissue (20, 40) and form an anastomosis (70). Cutting edge (776) is configured to cooperate with flat surface and a breakable washer (780) such that distal actuation of firing member (772) leads to the severing of tissue (20, 40) captured between cutting edge (776) and washer (780). Washer (780) may be any suitable shape and may be divided into any suitable number of pieces in order to accommodate the folding of coupling halves (768) in accordance with the description herein.

FIGS. 35A-36C show an exemplary use of anvil (760) and stapling head assembly (770) in order to capture tissue (20, 40) together and then cooperatively staple and sever tissue (20, 40) to form an anastomosis (70). First as shown in FIG. 35A, anvil (760) may have halves (768) in the folded position in order to insert anvil (760) more easily through lumen (20). Once near the desired position, anvil (760) may be unfolded such that folding halves (768) pivot about pin (769) in order to suitably form flat surface (766) and radially facing surface (762). Shank (765) may be coupled with trocar (330) in accordance with the description herein and actuated to the position shown in FIG. 36A.

Figure 36A:
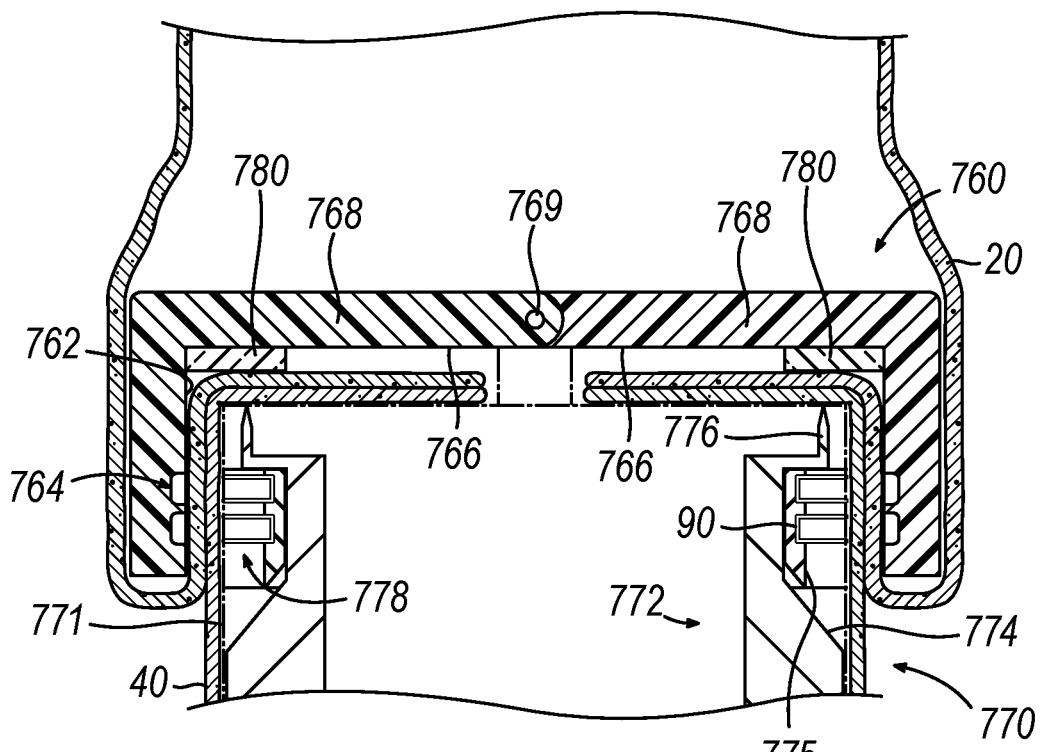
FIG. 36A depicts a cross-sectional view of the anvil of FIG. 34 coupled to the stapling head assembly of FIG. 34 in a pre-fired position.
Figure 36B:
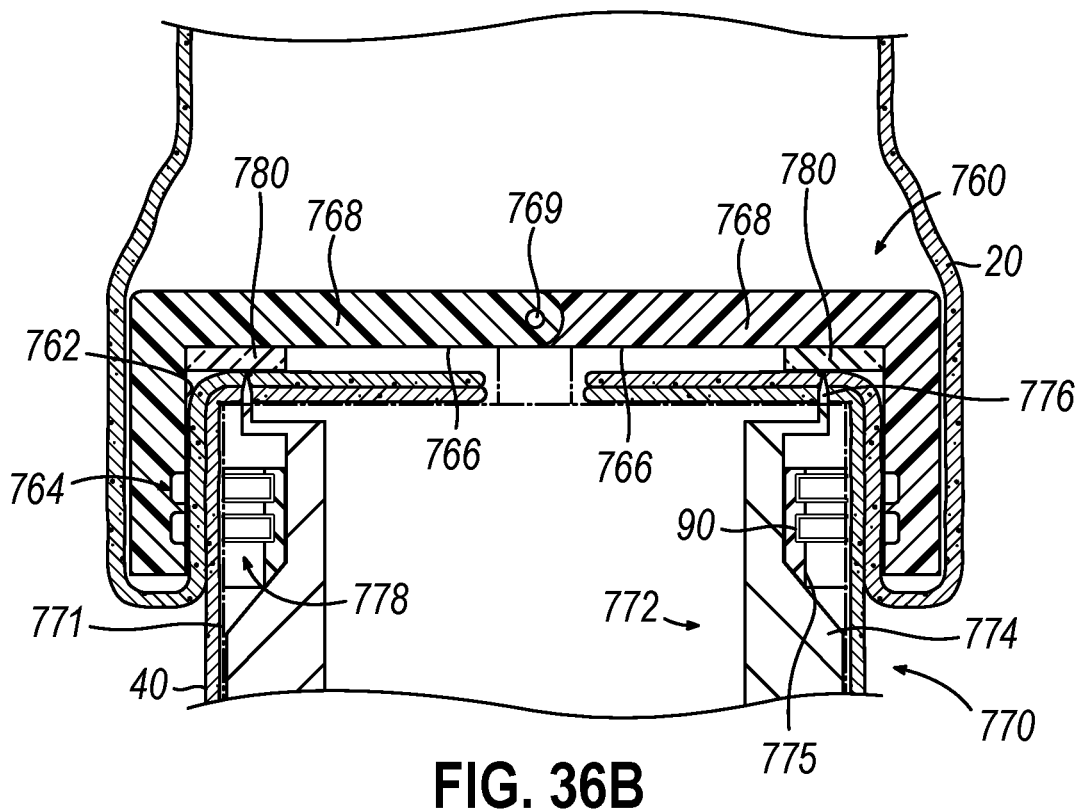
FIG. 36B depicts a cross-sectional view of the anvil of FIG. 34 coupled to the stapling head assembly of FIG. 34 in the middle of the firing processes.
Figure 36C:
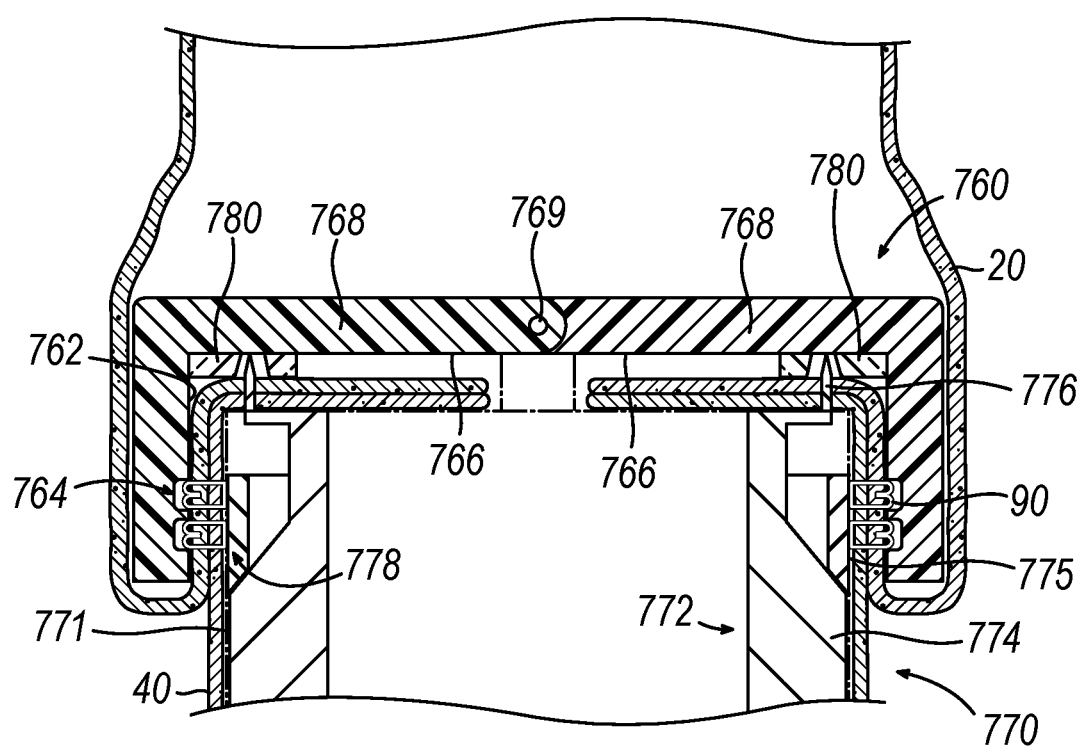
FIG. 36C depicts a cross-sectional view of the anvil of FIG. 34 coupled to the stapling head assembly of FIG. 34 completing the firing processes.
Figure 37A:
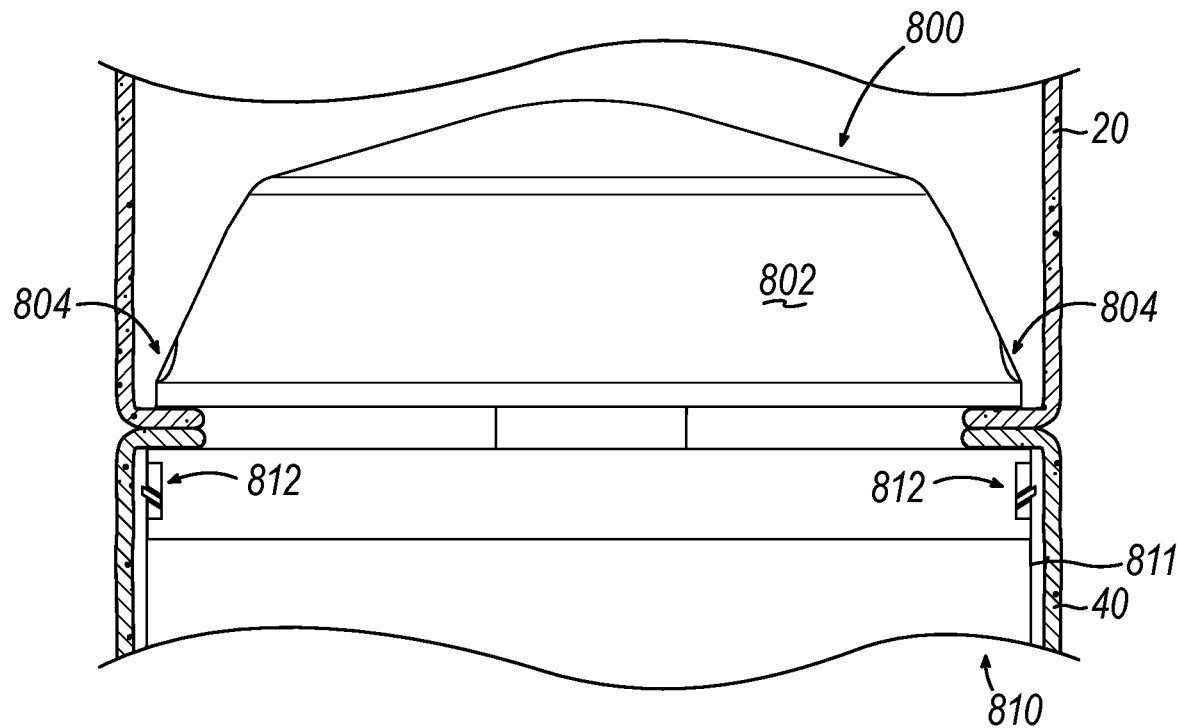
FIG. 37A depicts an elevational side view of an exemplary anvil and stapling head assembly that may be incorporated into the circular stapler of FIG. 1, the anvil and stapling head assembly grasping tissue lumens, in a pre-fired position.
Figure 37B:
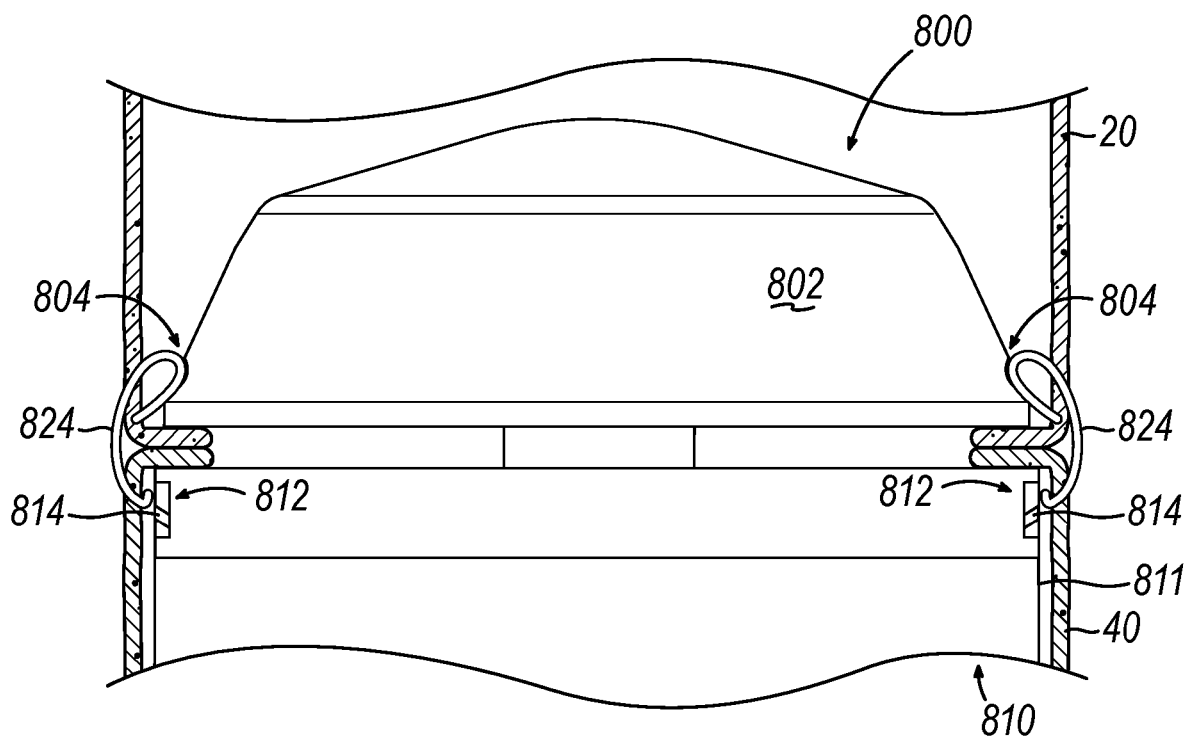
FIG. 37B depicts an elevational side view of the anvil and stapling head assembly of FIG. 37A in a post-fired position.

Once in the position shown in FIG. 36A, an operator may actuate firing member (772) in accordance with the description herein. As best shown in FIG. 36B, distal actuation of firing member (772) may allow cutting edge (776) to sever tissue (20, 40) that is between breakable washer (780) and a distal end of stapling head assembly (770). Next, as shown in FIG. 36C, further distal actuation of firing member (772) allows cam surface (774) of firing member (772) to abut against a complementary surface of staple drivers (775), thereby forcing staple drivers (775) radially outward toward tissue (20, 40) interposed between staple forming pockets (764) and the portion of cylindrical body (771) defining staple openings (778). In response, staples (90) are driven through tissue (20, 40), against staple forming pockets (765) and then back into tissue (20, 40) in order to staple tissue (20, 40) together, thereby leaving a newly formed anastomosis. The breaking of breakable washer (780) may signal to an operator that tissue has been severed and stapled in accordance with the description herein.

In some instances, it may be desirable to fire staples in the radial direction and deform such a staple on the outer surface of an anvil, rather than an inner surface of anvil. This may allow the size of anvil to be smaller than if staples were fired radially outward against an interior surface of anvil.

FIGS. 37A-38B show an anvil (800) and a stapling head assembly (810) configured to deform legs (824) of a staple (820) on an exterior surface (802) of anvil (800). Anvil (800) includes outer surface (802) defining a plurality of staple forming pockets (804). Staple forming pockets (804) are formed on the outer surface (802) of anvil (800) such that staple forming pockets (804) do not face toward a portion of stapling head assembly (810). As will be described in greater detail below, stapling head assembly (810) is configured to drive staples (820) along an arched path (818) such that even though staple openings (812) of stapling head assembly (810) do not face directly toward staple forming pockets (804), legs (824) of staples (820) deform against staple forming pockets (804).

Figure 38A:
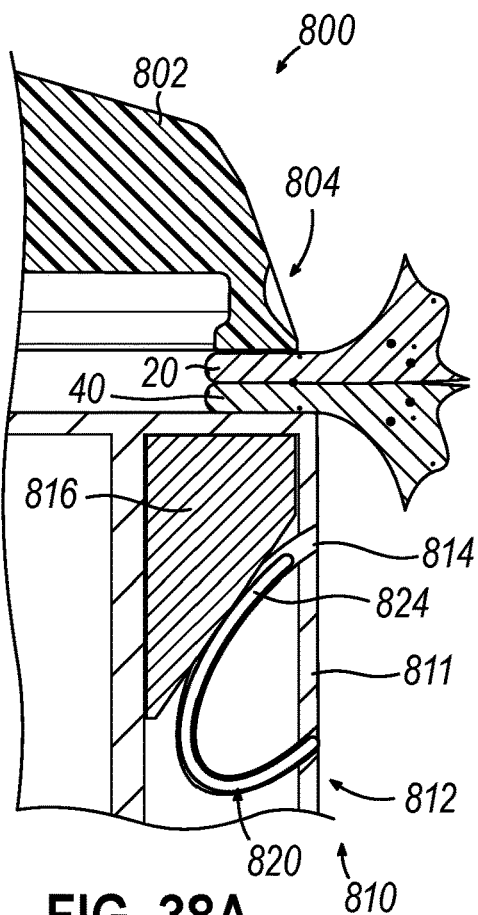
FIG. 38A depicts an enlarged cross-sectional view of the anvil and stapling head assembly of FIG. 37A in the pre-fired position.
Figure 38B:
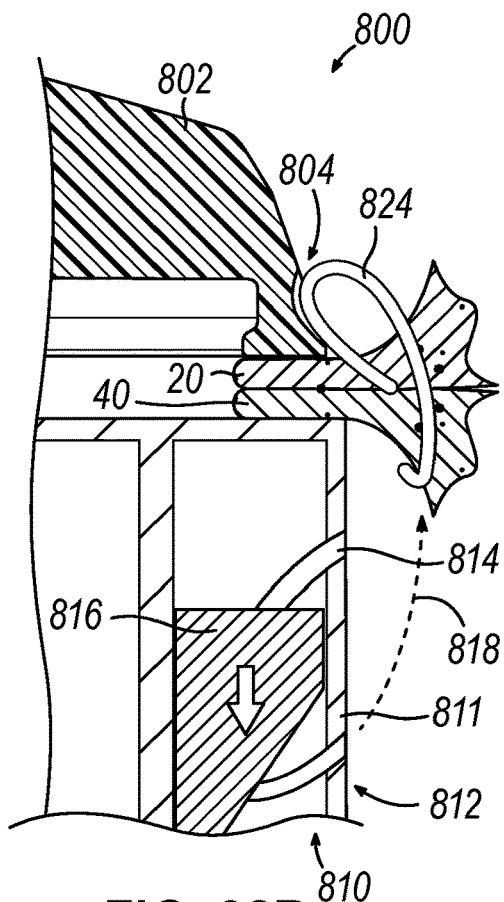
FIG. 38B depicts an enlarged cross-sectional view of the anvil and stapling head assembly of FIG. 37A in the post-fired position.
Figure 39:
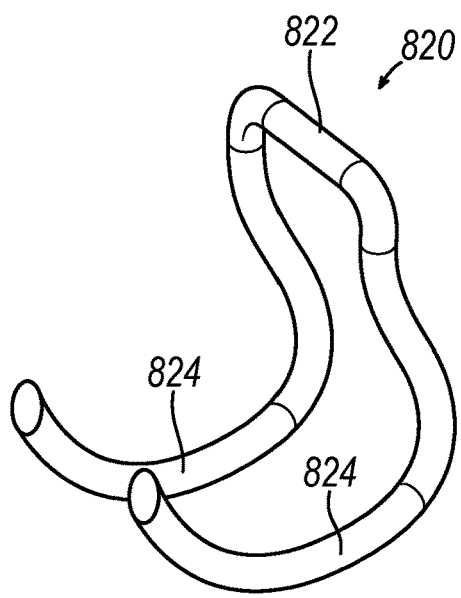
FIG. 39 depicts a perspective view of an exemplary staple configured to be used with the anvil and stapling head assembly of FIG. 37A.
Figure 40:
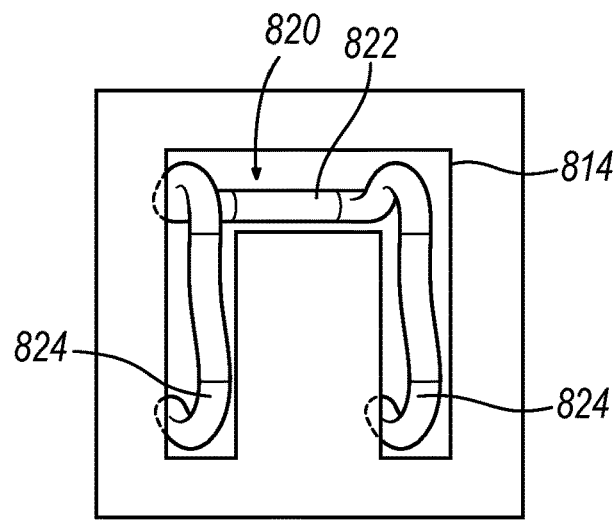
FIG. 40 depicts a perspective view of the staple of FIG. 39 housed within a staple guiding surface of the stapling head assembly of FIG. 37A.

As shown in FIGS. 38A-38B, stapling head assembly (810) includes a tubular body member (811) defining an annular array of radially presented staple openings (812). Tubular body member (811) also defines a staple guiding surface (814) extending from an interior of tubular body member (811) into each staple opening (812). Staple guiding surface (814) slidably houses staples (820) within staple openings (812). Staple guiding surface (814) is sufficiently arched to complement the arched profile of hooked legs (824) of staple (820) such that when staples (820) are driven out of staple openings (812) in accordance with the description herein, staples (820) travel along an arched path (818) to engage staple forming pockets (804) located on the outer surface (802) of anvil (800), thereby stapling tissue (20, 40) and shown in FIGS. 37B and 38B.

Stapling head assembly (810) also includes a staple driver (816). Staple driver (816) is configured to actual relative to tubular body member (811) in order to cam against crown (822) of staple (820) to thereby drive staples (820) along the path provided by staple guiding surface (814). In the current example, staple drive (816) has a slanted camming surface such that as staple (820) travels along the arched path provided by staple guiding surface (814), staple driver (816) may maintain suitable contact with crown (816). Any suitable mechanism may actuate staple driver (816) as would be apparent to one skilled in the art in view of the teachings herein.

As mentioned above, staple (820) includes a crown (822) and two C-style hooked legs (824) extending from respective ends of crown (822). C-style hooked legs (824) cooperatively engage staple guiding surface (814) in order to travel arched path (818) to thereby engage staple forming pockets (804) that face away from respective staple openings (812), rather than conventionally facing toward staple openings (812). This feature may allow anvil (400) to suitably deform staples (820) fired in a radial direction without having to increase the radial size of anvil (400).

In some instances, it may be desirable to sever tissue along a path that extends radially from a stapling head assembly that along a conventional path that extends parallel with the longitudinal axis of stapling head assembly (as done by stapling head assembly (300, 770). This may increase the diameter at which knife cuts tissue (20, 40), which may in turn reduce the size which severed edges (60) extends radially within lumens (20, 40).

Figure 41:
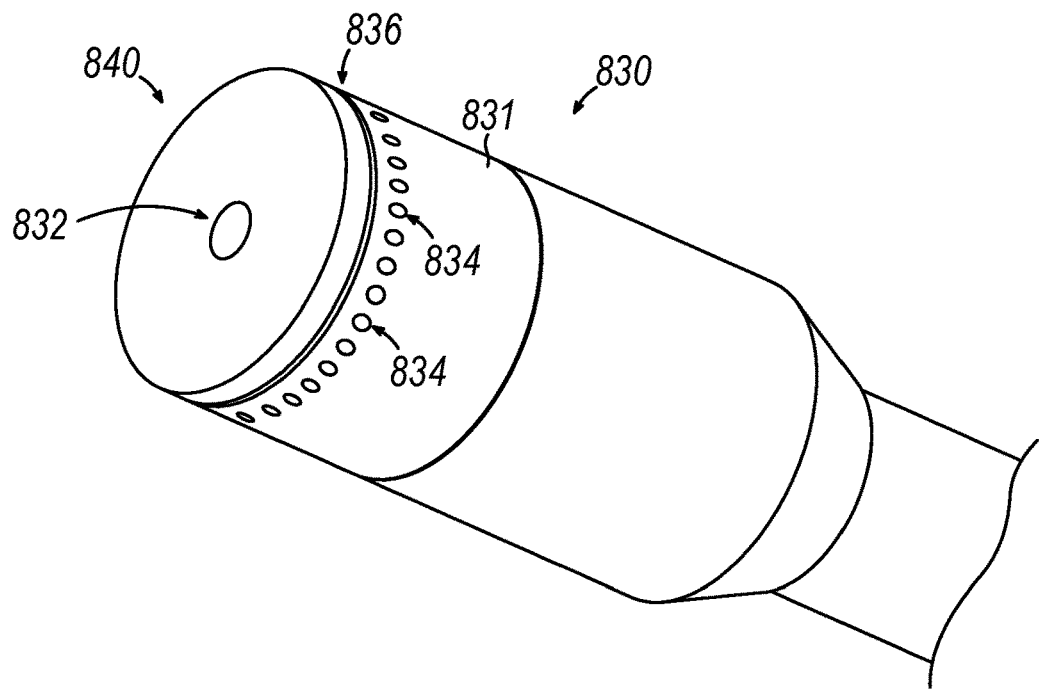
FIG. 41 depicts a perspective view of a stapling head assembly that may be incorporated into the circular stapler of FIG. 1, the stapling head assembly being configured to sever tissue with a radially retractable blade.
Figure 42:
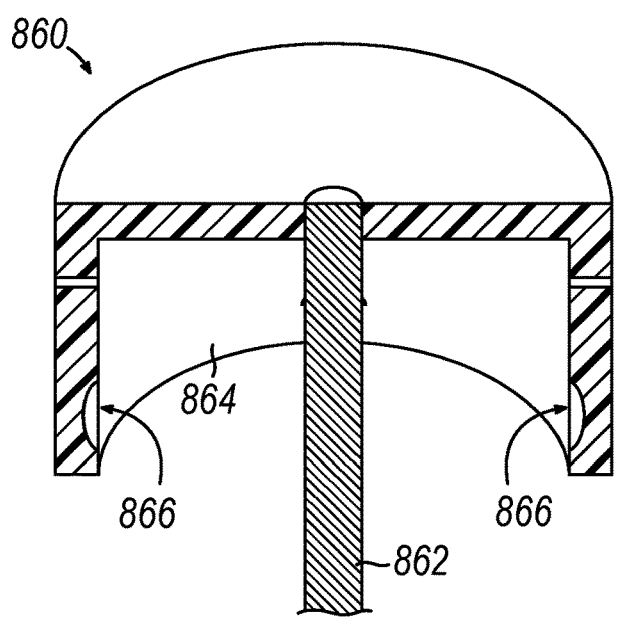
FIG. 42 depicts a cross-sectional view of an anvil configured to couple with the stapling head assembly of FIG. 41.

FIG. 41 shows a stapling head assembly (830) that includes a radial cutting assembly (840) configured to sever tissue captured against a tubular body (831) of stapling head assembly (831) above staple openings (834). Stapling head assembly (830) is configured to drive staples out of staple opening (834) in the radial direction away from tubular body (831) against staple forming pocket (866) (see FIG. 42) of an anvil (860). Stapling head assembly (830) includes an opening (832) dimensioned to couple with a shank (862) of anvil (860). Anvil (860) includes a radially facing surface (864 configured to face toward the exterior surface of tubular body (831) when coupled with stapling head assembly (830). In particular, radially facing surface (864) of anvil (864) is configured to face tubular body (831) such that staple openings (834) align with stapling forming pockets (866). Therefore, when staples are driven radially out of staple opening (834), staples with be driven through tissue and against a respective staple forming pocket (866) to thereby staple tissue.

Stapling head assembly (830) also defines a radially presented severing slot (836) dimensioned to allow a retractable blade (842) of radial cutting assembly (840) to extend through. Retractable blade (842) may extend out of radially presented severing slot (836) in order to circumferentially cut tissue captured between tubular body (831) and a portion of surface (864) located distally above staple forming pockets (866). As will be described in greater detail below, retractable blade (842) may selectively extend out of slot (836) and back within slot (836) in order to sever tissue in accordance with the tissue herein.

Figure 43A:
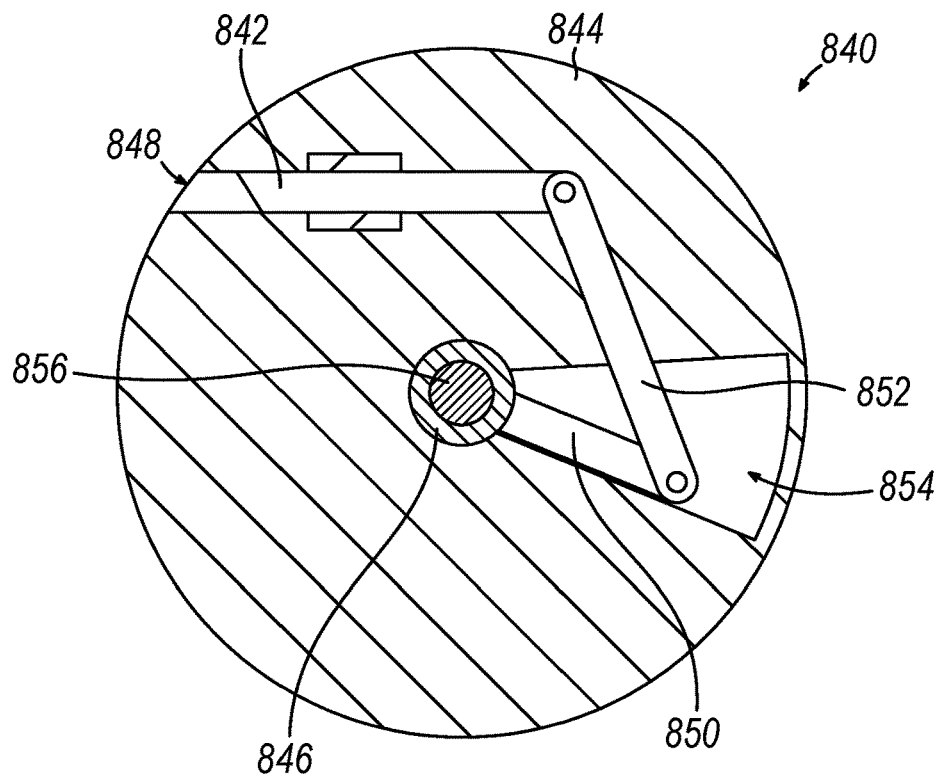
FIG. 43A depicts a cross-sectional view of a cutting assembly of the stapling head assembly of FIG. 41, with a radially retractable blade in a retracted position.
Figure 43B:
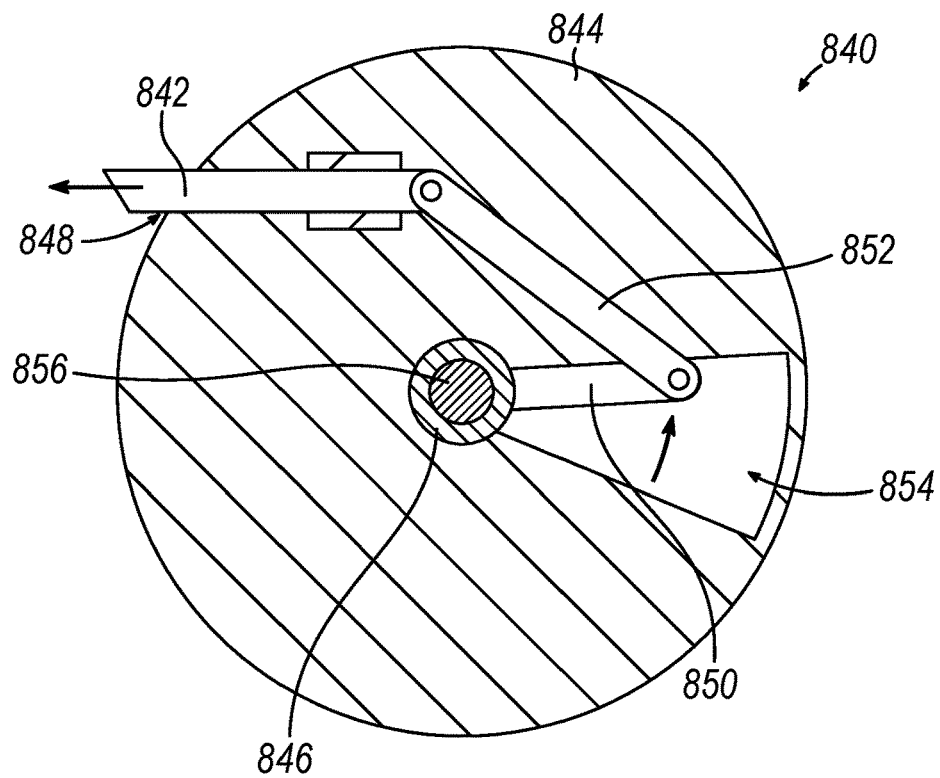
FIG. 43B depicts a cross-sectional view of the cutting assembly of FIG. 43A with the radially retractable blade in an extended position.
Figure 43C:
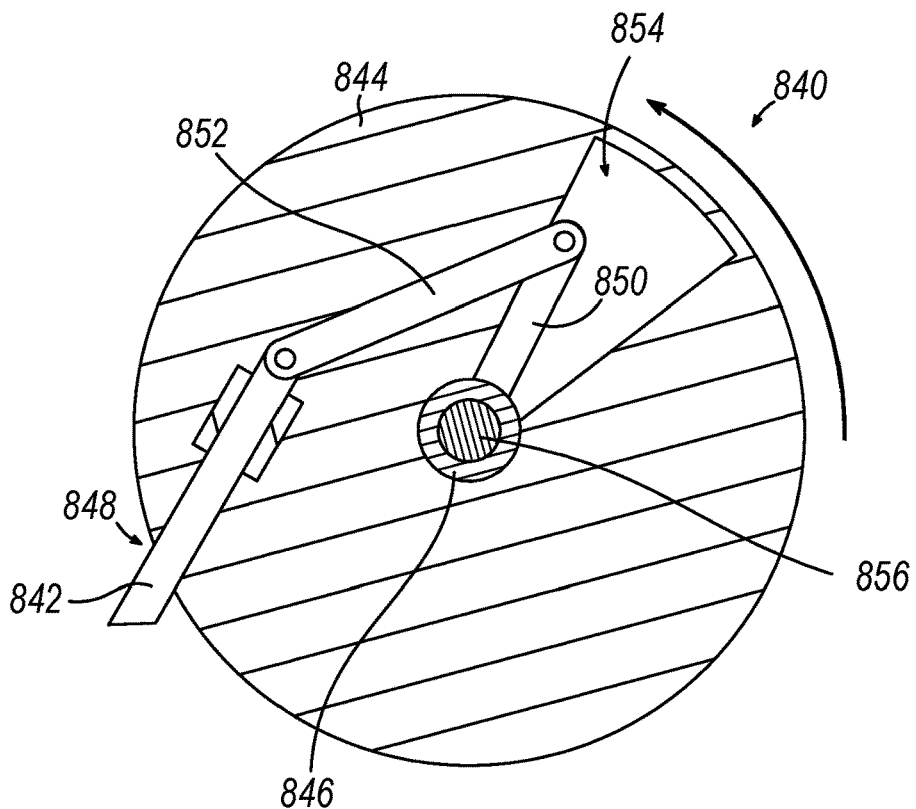
FIG. 43C depicts a cross-sectional view of the cutting assembly of FIG. 43A with the radially retractable blade in the extended position and rotated.
Figure 43D:
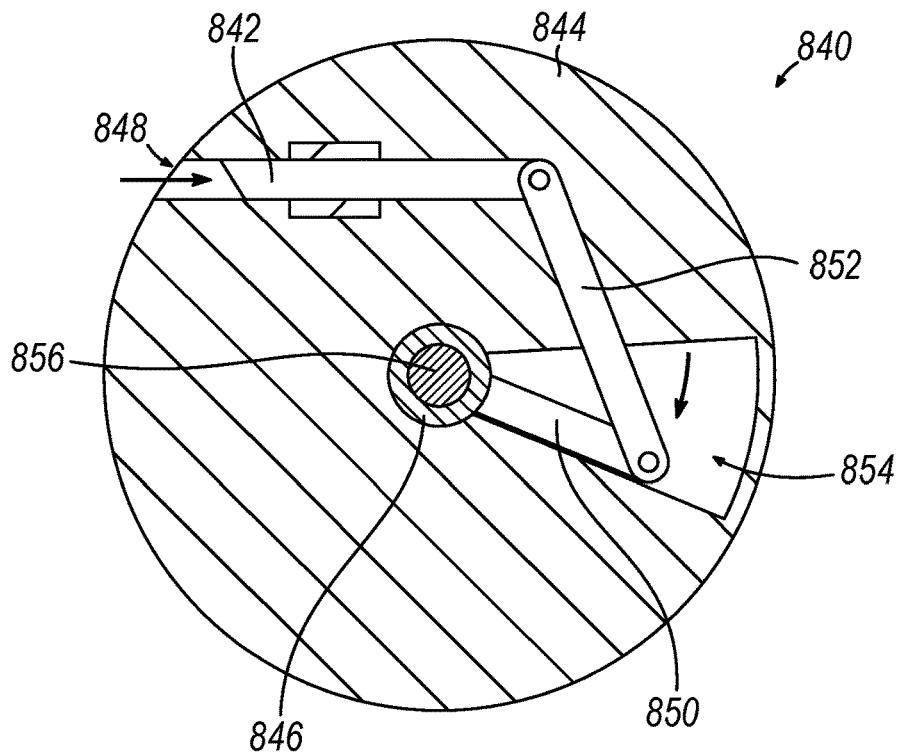
FIG. 43D depicts a cross-sectional view of the cutting assembly of FIG. 43A with the radially retractable blade in the retracted extended position after being rotated.

FIGS. 43A-43 show the various components of radial cutting assembly (840) and how radial cutting assembly (840) drives retractable blade (842) between the retracted position (see FIGS. 43A and 43D) and the extended position (see FIGS. 43B and 43C). It should be understood that while blade (842) is in the extended position, blade (842) may extend radially out of severing slot (836) in order to engage and sever tissue. It should also be understood that when blade is in the retracted position, blade (842) is prevented from engagement with tissue, thereby preventing inadvertent damage to tissue.

Radial cutting assembly (840) includes retractable blade (842), a rotatable blade housing (844), a rotating shaft (846), a first link (850) attached to rotating shaft (846), a second link (852) pivotally attached to first link (850) and retractable blade (840), and a drive shaft (856). Drive shaft (856) may rotate about its own longitudinal axis in order to rotate the entirety of radial cutting assembly (840) relative to the rest of stapling head assembly (830). Rotatable blade housing (844) defines a blade guide slot (848) and a link recess (854). Blade guide slot (848) slidably receives retractable blade (842) in order to guide blade (842) along the path between the retracted position and the extended position. link recess (854) provides adequate room for links (850, 852) to move in order to drive blade (842) along the path defined by blade guide slot (848).

Rotating shaft (846) is configured to be rotated about its own longitudinal axis in order to pivot first link (850) and second link (852) to thereby drive translation of retractable blade (840) between the retracted position and the extended position. Therefore, rotating shaft (846) may rotate in a first rotational direction to drive blade (842) into the extended position; while rotating shaft (846) may also rotate in a second rotational direction to drive blade (842) into the retracted position. First link (850) has one end directly attached to rotating shaft (846) such that rotation of rotating shaft (846) drives rotation of first link (850) about the longitudinal axis of rotating shaft (846). Second link (852) is pivotally coupled to ends of both first link (850) and blade (842). Therefore, when first link (850) rotates, second link (852) translate and rotates in order to drive translation of blade ((850).

As best shown between FIGS. 43A-43B, when it is suitable for blade (842) to actuate from the retracted position to the extended position, rotating shaft (846) may rotate in the first rotational direction. Therefore, first link (850) rotates within link recess (854), while second link (852) rotates and translates within link recess (854), thereby driving translation of blade within blade guide slot (848) into the extended position. With blade (842) in the extended position, as shown between FIGS. 43B-43C, drive shaft (856) may be rotated about its own longitudinal axis, thereby rotating the entirely of cutting assembly (840), including blade (842). Since blade (842) is exposed in the extended position, blade (842) may sever tissue captured between radially facing surface (864) of anvil (860) and tubular body (831) of stapling head assembly (830).

Once blade (842) has been suitable rotate to completely sever tissue, blade (842) may then be retracted by rotating shaft (846) in the second rotational direction in accordance with the description above, thereby actuating blade (842) into the retracted position.

III. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) an anvil defining a plurality of staple forming pockets; and (b) a stapling head assembly comprising: (i) a body, (ii) a coupling member configured to actuate relative to the body to thereby acuate the anvil relative to the body, (iii) a firing assembly configured to drive a plurality of staples against the staple forming pockets of the anvil, and (iv) a staple deck defined by an outer arched perimeter and an inner arched perimeter fixed to the body, wherein the staple deck defines a plurality of staple openings, wherein at least one non-tangential staple opening in the plurality of staple openings extends along a longitudinal axis in a non-tangential relationship with a closest tangent line of the inner arched perimeter or the outer arched perimeter.

Example 2

The surgical stapling instrument of Example 1, wherein the closest tangent line is measured from a distance between a center point of the at least one non-tangential staple opening and the inner arched perimeter.

Example 3

The surgical stapling instrument of any of Examples 1 through 2, wherein the plurality of staple openings comprises an outer array of staple openings and an inner array of staple openings.

Example 4

The surgical stapling instrument of Example 3, wherein the plurality of staple openings further comprises an intermediate array of staple openings located radially between the outer array of staple openings and the inner array of staple openings.

Example 5

The surgical stapling instrument of any of Examples 1 through 4, wherein the plurality of staple openings comprises a first group of staple openings and a second group of staple openings, each staple opening of the first group having a first length, each staple opening of the second group having a second length.

Example 6

The surgical stapling instrument of Example 5, wherein the first length is different than the second length.

Example 7

The surgical stapling instrument of any of Examples 1 through 6, wherein the non-tangential relationship comprises the at least one non-tangential staple opening extending along an axis forming a 40-degree angle with closest tangent line of the inner arched perimeter.

Example 8

The surgical stapling instrument of any of Examples 1 through 7, wherein the non-tangential relationship comprises the at least one non-tangential staple opening extending along an axis forming a 45-degree angle with closest tangent line of the inner arched perimeter.

Example 9

The surgical stapling instrument of any of Examples 1 through 8, wherein at least one tangential staple opening in the plurality of staple openings extends in a tangential relationship with the closest tangent line of the inner arched perimeter or the outer arched perimeter.

Example 10

The surgical stapling instrument of any of Examples 1 through 9, wherein at least one staple in the plurality of staples comprises a pair of legs and a crown, wherein the crown comprises an upward bend extension in a direction toward a tip of a of the pair of legs.

Example 11

The surgical stapling instrument of any of Examples 1 through 10, wherein at least one staple in the plurality of staples comprises a pair of legs and a crown, wherein the crown comprises an upward bend extension in a direction away a tip of a of the pair of legs.

Example 12

The surgical stapling instrument of any of Examples 1 through 11, wherein the firing assembly comprises a plurality of staple drivers and a cutting edge unitarily attached to the plurality of staple drivers.

Example 13

The surgical stapling instrument of any of Examples 1 through 12, wherein the staple deck defines an annular shape.

Example 14

The surgical stapling instrument of any of Examples 1 through 13, wherein the coupling member is configured to selectively couple with the anvil.

Example 15

The surgical stapling instrument of Example 14, wherein the coupling member comprises a trocar, wherein the anvil comprise a shank configured to selectively couple with the trocar.

Example 16

A surgical stapling instrument, comprising: (a) an anvil defining a plurality of staple forming pockets; and (b) a stapling head assembly comprising: (i) a body, (ii) a coupling member configured to selectively coupled with the anvil, wherein the coupling member is configured to actuate relative to the body to thereby acuate the anvil relative to the body, (iii) a firing assembly configured to drive a plurality of staples against the staple forming pockets of the anvil, and (iv) a staple deck defining a plurality of staple openings, wherein the staple deck is configured to actuate in a radial direction relative to the body in order to define a gap distance with the anvil.

Example 17

The surgical stapling instrument of Example 16, wherein the staple deck comprises a plurality of resilient bodies.

Example 18

The surgical stapling instrument of any of Examples 16 through 17, wherein the staple deck comprises a plurality of translating bodies.

Example 19

The surgical stapling instrument of any of Examples 16 through 18, wherein the anvil comprises a radially facing surface configured to define the gap distance with the staple deck.

Example 20

A surgical stapling instrument, comprising: (a) an anvil defining a plurality of staple forming pockets; and (b) a stapling head assembly comprising: (i) a body, (ii) a coupling member configured to selectively coupled with the anvil, wherein the coupling member is configured to actuate relative to the body to thereby acuate the anvil relative to the body, (iii) a staple deck defining a plurality of staple openings, and (vi) a firing assembly configured to drive a plurality of staples in a radial direction against the staple forming pockets of the anvil.

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/041,391, entitled "Methods of Forming an Anastomosis Between Organs with an Expandable Staple Pattern," filed on Aug. 13, 2021; U.S. patent application Ser. No. 17/401,428, entitled "Staple Forming Features for Circular Surgical Stapler," filed on Aug. 13, 2021; U.S. patent application Ser. No. 17/401,430, entitled "Non-Circular End Effector Features for Circular Surgical Stapler," filed on Aug. 13, 2021; U.S. patent application Ser. No. 17/401,439, entitled "Circular Surgical Stapler End Effector Having Staple Line Alignment Feature," filed on Aug. 13, 2021; U.S. patent application Ser. No. 17/401,451, entitled "Circular Surgical Stapler Having Staples with Expandable Crowns," filed on Aug. 13, 2021; and U.S. patent application Ser. No. 17/401,460, entitled "Circular Surgical Stapler for Forming Cross-Pattern of Staples," filed on Aug. 13, 2021. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:
   (a) an anvil defining a plurality of staple forming pockets; and
   (b) a stapling head assembly comprising:
      (i) a body,
      (ii) a coupling member configured to actuate relative to the body to thereby actuate the anvil relative to the body,
      (iii) a firing assembly configured to drive a plurality of staples against the staple forming pockets of the anvil, and
      (iv) a staple deck defined by an outer arched perimeter and an inner arched perimeter fixed to the body, wherein the staple deck defines a plurality of staple openings, wherein at least one non-tangential staple opening in the plurality of staple openings extends along a longitudinal axis in a non-parallel relationship with a closest tangent line of the inner arched perimeter or the outer arched perimeter, wherein the plurality of staple openings comprises a first group of staple openings and a second group of staple openings, each staple opening of the first group having a first length, each staple opening of the second group having a second length.

2. The surgical stapling instrument of claim 1, wherein the closest tangent line is measured from a distance between a center point of the at least one non-tangential staple opening and the inner arched perimeter.

3. The surgical stapling instrument of claim 1, wherein the plurality of staple openings comprises an outer array of staple openings and an inner array of staple openings.

4. The surgical stapling instrument of claim 3, wherein the plurality of staple openings further comprises an intermediate array of staple openings located radially between the outer array of staple openings and the inner array of staple openings.

5. The surgical stapling instrument of claim 1, wherein the first length is different than the second length.

6. The surgical stapling instrument of claim 1, wherein the non-tangential relationship comprises the at least one non-tangential staple opening extending along an axis forming a 40-degree angle with closest tangent line of the inner arched perimeter.

7. The surgical stapling instrument of claim 1, wherein the non-tangential relationship comprises the at least one non-tangential staple opening extending along an axis forming a 45-degree angle with closest tangent line of the inner arched perimeter.

8. The surgical stapling instrument of claim 1, wherein at least one tangential staple opening in the plurality of staple openings extends in a tangential relationship with the closest tangent line of the inner arched perimeter or the outer arched perimeter.

9. The surgical stapling instrument of claim 1, wherein at least one staple in the plurality of staples comprises a pair of legs and a crown, wherein the crown comprises an upward bend extension in a direction toward a tip of a of the pair of legs.

10. The surgical stapling instrument of claim 1, wherein at least one staple in the plurality of staples comprises a pair of legs and a crown, wherein the crown comprises an upward bend extension in a direction away a tip of a of the pair of legs.

11. The surgical stapling instrument of claim 1, wherein the firing assembly comprises a plurality of staple drivers and a cutting edge unitarily attached to the plurality of staple drivers.

12. The surgical stapling instrument of claim 1, wherein the staple deck defines an annular shape.

13. The surgical stapling instrument of claim 1, wherein the coupling member is configured to selectively couple with the anvil.

14. The surgical stapling instrument of claim 13, wherein the coupling member comprises a trocar, wherein the anvil comprise a shank configured to selectively couple with the trocar.

15. A surgical stapling instrument, comprising:
   (a) an anvil defining a plurality of staple forming pockets; and
   (b) a stapling head assembly comprising:
      (i) a body,
      (ii) a coupling member configured to selectively coupled with the anvil, wherein the coupling member is configured to actuate relative to the body to thereby actuate the anvil relative to the body,
      (iii) a firing assembly configured to drive a plurality of staples against the staple forming pockets of the anvil, and
      (iv) a staple deck defining a plurality of staple openings, wherein the staple deck is configured to actuate in a radial direction relative to the body in order to define a gap distance with the anvil.

16. The surgical stapling instrument of claim 15, wherein the staple deck comprises a plurality of resilient bodies.

17. The surgical stapling instrument of claim 15, wherein the staple deck comprises a plurality of translating bodies.

18. The surgical stapling instrument of claim 15, wherein the anvil comprises a radially facing surface configured to define the gap distance with the staple deck.

19. A surgical stapling instrument, comprising:
   (a) an anvil defining a plurality of staple forming pockets; and
   (b) a stapling head assembly comprising:
      (i) a body,
      (ii) a coupling member configured to selectively coupled with the anvil, wherein the coupling member is configured to actuate relative to the body to thereby actuate the anvil relative to the body,
      (iii) a staple deck defining a plurality of staple openings, and
      (vi) a firing assembly configured to drive a plurality of staples in a radial direction against the staple forming pockets of the anvil.

* * * * *